United States Patent [19]
Borromeo et al.

[11] Patent Number: 5,646,111
[45] Date of Patent: Jul. 8, 1997

[54] CYCLIC PEPTIDE ANTIFUNGAL AGENTS

[75] Inventors: Peter S. Borromeo, Fishers; James A. Jamison; Michael J. Rodriguez, both of Indianapolis; William W. Turner, Bloomington; Venkatraghaven Vasudevan, Indianapolis, all of Ind.

[73] Assignee: Eli Lilly and Company, Indianapolis, Ind.

[21] Appl. No.: 612,208

[22] Filed: Mar. 7, 1996

Related U.S. Application Data

[63] Continuation of Ser. No. 418,341, Apr. 7, 1995, abandoned.
[51] Int. Cl.$^6$ .................. C07K 7/64; C07K 7/50
[52] U.S. Cl. .................. 514/11; 514/7; 530/317
[58] Field of Search ............... 530/317; 514/9.11

[56] References Cited

U.S. PATENT DOCUMENTS

| | | |
|---|---|---|
| 4,293,488 | 10/1981 | Debono . |
| 4,293,489 | 10/1981 | Debono . |
| 4,320,052 | 3/1982 | Abbott et al. . |
| 5,166,135 | 11/1992 | Schmatz . |

FOREIGN PATENT DOCUMENTS

| | | |
|---|---|---|
| 359529 | 3/1990 | European Pat. Off. . |
| 447186 | 9/1991 | European Pat. Off. . |
| 448343 | 9/1991 | European Pat. Off. . |
| 448353 | 9/1991 | European Pat. Off. . |
| 448354 | 9/1991 | European Pat. Off. . |
| 448355 | 9/1991 | European Pat. Off. . |
| 448356 | 9/1991 | European Pat. Off. . |
| 462531 | 12/1991 | European Pat. Off. . |
| 0486011A3 | 5/1992 | European Pat. Off. . |
| 0 486 011A3 | 5/1992 | European Pat. Off. . |
| 503960 | 9/1992 | European Pat. Off. . |
| 525889 | 2/1993 | European Pat. Off. . |
| 0561639 | 9/1993 | European Pat. Off. . |
| 561639 | 9/1993 | European Pat. Off. . |
| 2241956 | 9/1991 | United Kingdom . |
| 2242194 | 9/1991 | United Kingdom . |

*Primary Examiner*—Howard E. Schain
*Attorney, Agent, or Firm*—Janet T. McClain; David E. Boone

[57] ABSTRACT

Provided are pharmaceutical formulations, and methods of inhibiting fungal and parasitic activity using a compound of formula I:

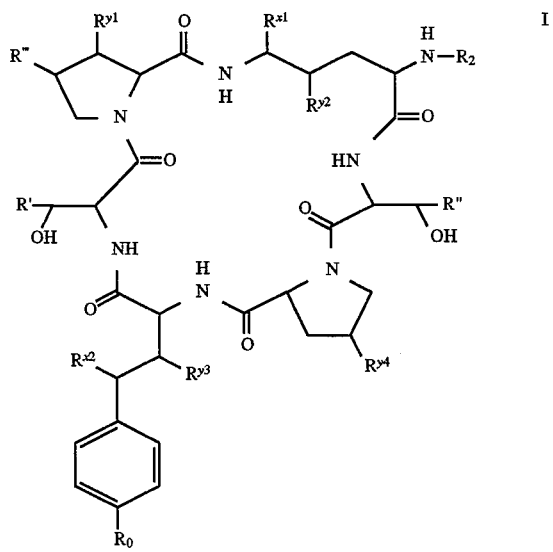

wherein:

R' is hydrogen, methyl or $NH_2C(O)CH_2$—;

R" and R''' are independently methyl or hydrogen;

$R^{x1}$, $R^{x2}$, $R^{y1}$, $R^{y2}$, $R^{y3}$, and $R^{y4}$ are independently hydroxy or hydrogen;

$R_0$ is a group of the formula

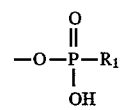

$R_1$ is $C_1$–$C_6$ alkyl, $C_1$–$C_6$ alkoxy, phenyl, p-halo-phenyl, p-nitrophenyl, phenoxy, benzyl, p-halo-benzyl, or p-nitro-benzyl; and $R_2$ is an acyl side chain as defined herein.

64 Claims, No Drawings

CYCLIC PEPTIDE ANTIFUNGAL AGENTS

This application is a continuation of application Ser. No. 08/418,341, filed on Apr. 7, 1995 now abandoned.

BACKGROUND OF THE INVENTION

This invention relates to semi-synthetic cyclic peptide compounds which are useful as antifungal and antiparasitic agents and which have improved stability and water solubility. In particular, it relates to derivatives of the echinocandin class of cyclic peptides; to methods for treating fungal and parasitic infections, and to formulations useful in the methods.

The compounds provided by this invention are semi-synthetic compounds derived from cyclic peptides which are produced by culturing various microorganisms. A number of cyclic peptides are known in the art including echinocandin B (A30912A), aculeacin, mulundocandin, sporiofungin, L-671,329, and S31794/F1.

In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R_2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489). Among such antifungal agents is cilofungin which is represented by a compound of formula I where R', R", and R'" are methyl; $R^{x1}$ and $R^{x2}$ are hydroxy, $R^{y1}$, $R^{y2}$, $R^{y3}$, $R^{y4}$ are hydroxy, $R_0$ is hydroxy, and $R_2$ is p-(octyloxy) benzoyl.

SUMMARY OF THE INVENTION

The present invention provides a compound of formula I:

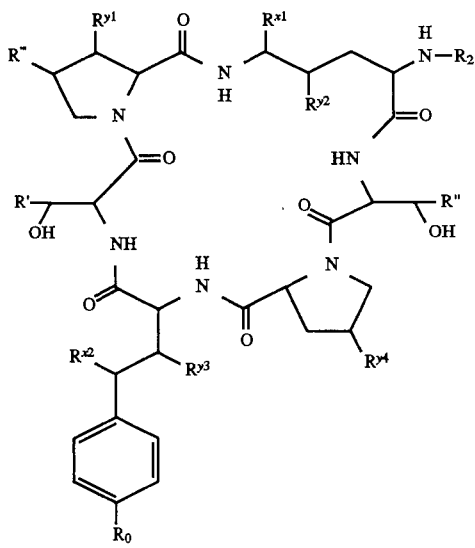

wherein:

R' is hydrogen, methyl or $NH_2C(O)CH_2$—;

R" and R'" are independently methyl or hydrogen;

$R^{x1}$, $R^{x2}$, $R^{y1}$, $R^{y2}$, $R^{y3}$, and $R^{y4}$ are independently hydroxy or hydrogen;

$R_0$ is a group of the formula

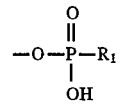

$R_1$ is $C_1$–$C_6$ alkyl, $C_1$–$C_6$ alkoxy, phenyl, p-halo-phenyl, p-nitrophenyl, phenoxy, benzyl, p-halo-benzyl, or p-nitro-benzyl;

I) $R_2$ is a group of the formula

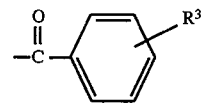

where:

A) $R_3$ is $C_1$–$C_{12}$ alkyl, $C_1$–$C_6$ alkoxy or quinolyl;

B) $R_3$ is —O—$(CH_2)_m$—[O—$(CH_2)_n]_p$—O—($C_1$–$C_{12}$ alkyl);

m and n are independently 2, 3 or 4;

p is 0 or 1; or

C) $R_3$ is —Y—($C_1$–$C_{12}$ alkyl);

Y is —C≡C— or —CH=CH—; or

D) $R_3$ is —O—$(CH_2)_q$—G;

q is 2, 3 or 4;

G is $C_7$–$C_{10}$ bicycloalkyl or $C_7$–$C_{14}$ tricycloalkyl; or

II) $R_2$ is a group of the formula

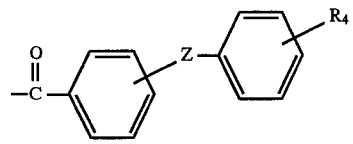

where:

Z is —O—, —C≡C—, —CH=CH—, —$CH_2$—$CH_2$—, —$CH_2$—, or a bond;

A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or phenyl substituted with a group of the formula —O—$(CH_2)_m$—[O—$(CH_2)_n]_p$—O—($C_1$–$C_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_t$ tricycloalkyl, $C_1$–$C_6$ alkoxy, $C_2$–$C_{12}$ alkynyl, amino, $C_1$–$C_4$ alkylamino, di ($C_1$–$C_4$ alkyl)amino, formamido, $C_2$–$C_{12}$ alkanoylamino, or phenyl substituted with a group of the formula —O—$(CH_2)_m$—[O—$(CH_2)_n]_p$—O—($C_1$–$C_{12}$ alkyl) where m, n and p are as defined above; or D) $R_4$ is —O—(CH$_2$)$_r$—W—R$_5$;
   r is 2, 3 or 4;
   W is pyrrolidino, piperidino or piperazino;
   $R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —Y$^1$—R$_6$;
   y$^1$ is —C≡C— or —CH=CH—;
   $R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—(CH$_2$)$_r$—W—R$_5$ where r, W and $R_5$ are as defined above; or
   $R_6$ is phenyl substituted with a group of the formula —O—(CH$_2$)$_m$—[O—(CH$_2$)$_n$]$_p$—O—($C_1$–$C_{12}$ alkyl) where m, n and p are as defined above; or F) $R_4$ is $C_1$–$C_{12}$ alkoxy substituted with a group of the formula —NHC(O)R$_7$;
   $R_7$ is $C_1$–$C_6$ alkoxy, or phenyl($C_1$–$C_6$ alkoxy); or III) $R_2$ is a group of the formula

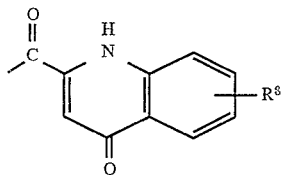

where R$^8$ is $C_1$–$C_{12}$ alkoxy or a group of the formula —O—(CH$_2$)$_m$—[O—(CH$_2$)$_n$]$_p$—O—($C_1$–$C_{12}$ alkyl) where m, n and p are as defined above; or IV) $R_2$ is a group of the formula

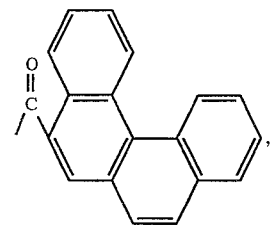

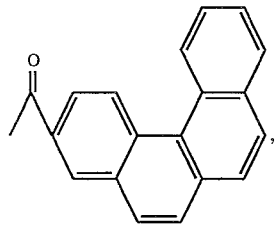

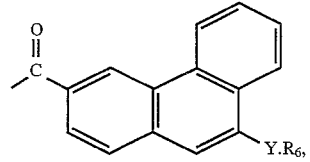

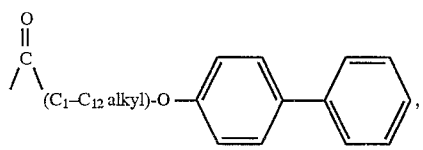

-continued
or

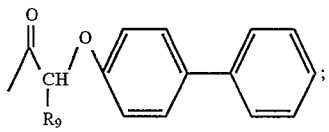

where:
   Y and $R_6$ are as defined above;
   $R_9$ is phenyl, $C_1$–$C_{12}$ alkyl, or $C_1$–$C_{12}$ alkoxy; or V) $R_2$ is naphthoyl substituted with $R_4$ where $R_4$ is as defined above;

or a pharmaceutically acceptable salt thereof.

Also provided are pharmaceutical formulations, methods for inhibiting parasitic or fungal activity and methods of treating fungal or parasitic infections which employ the compounds of the invention.

DETAILED DESCRIPTION

As used herein, the term "$C_1$–$C_{12}$ alkyl" refers to a straight or branched alkyl chain having from one to twelve carbon atoms. Typical $C_1$–$C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1$–$C_{12}$ alkyl" includes within its definition the terms "$C_1$–$C_6$ alkyl" and $C_1$–$C_4$ alkyl."

The term "halo" refers to chloro, fluoro, bromo or iodo.

The term "$C_2$–$C_{12}$ alkenyl" refers to a straight or branched alkenyl chain having from two to twelve carbon atoms. Typical $C_2$–$C_{12}$ alkenyl groups include ethenyl, 1-propen-2-yl, 3-buten-1-yl, 1-buten-2-yl, 1-buten-1-yl, 1-penten-3-yl, 2-hexen-3-yl, 1-decen-2-yl, 2-decen-5-yl and the like.

The term "$C_2$–$C_{12}$ alkynyl" refers to a straight or branched alkynyl chain having from two to twelve carbon atoms. Typical $C_2$–$C_{12}$ alkynyl groups include ethynyl, 1-propyn-1-yl, 1-propyn-2-yl, 1-butyn-1-yl, 1-butyn-3-yl, 1-pentyn-3-yl, 4-pentyn-2-yl, 1-hexyn-3-yl, 3-hexyn-1-yl, 5-methyl-3-hexyn-1-yl, 5-octyn-1-yl, 7-octyn-1-yl, 4-decyn-1-yl, 6-decyn-1-yl and the like.

The term "$C_1$–$C_{12}$ alkylthio" refers to a straight or branched alkyl chain having from one to twelve carbon atoms attached to a sulfur atom. Typical $C_1$–$C_{12}$ alkylthio groups include methylthio, ethylthio, propylthio, isopropylthio, butylthio, 3-methyl-heptylthio, octylthio, 5,5-dimethyl-hexylthio and the like.

The term "$C_1$–$C_{12}$ alkoxy" refers to a straight or branched alkyl chain having from one to twelve carbon atoms attached to an oxygen atom. Typical $C_1$–$C_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "$C_1$–$C_{12}$ alkyl" includes within its definition the terms "$C_1$–$C_6$ alkoxy" and $C_1$–$C_4$ alkoxy."

The terms "$C_1$–$C_{12}$ substituted alkyl," "$C_2$–$C_{12}$ substituted alkenyl" and "$C_2$–$C_{12}$ substituted alkynyl," refers to the specified moiety substituted with 1 or 2 substituents independently selected from halo, hydroxy, protected hydroxy, amino, protected amino, $C_1$–$C_7$ acyloxy, nitro, carboxy, protected carboxy, carbamoyl, carbamoyloxy, cyano, methylsulfonylamino, phenyl, substituted phenyl or $C_1$–$C_{12}$ alkoxy.

The term "substituted phenyl" refers to a phenyl group substituted with 1, 2 or 3 substituents independently selected from halo, hydroxy, protected hydroxy, cyano, nitro, $C_1$–$C_{12}$ alkyl, $C_1$–$C_{12}$ alkoxy, carboxy, protected carboxy, carbomymethyl, hydroxymethyl, amino, aminomethyl trifluoromethyl or N-methylsulfonylamino.

The term "$C_3$–$C_{12}$ cycloalkyl" refers a saturated hydrocarbon ring structure having from three to twelve carbon atoms. Typical $C_3$–$C_{12}$ cycloalkyl groups include cyclopropyl, cyclobutyl, cyclopentyl, cyclohexyl and cycloheptyl, cyclooctyl and the like.

The term "$C_3$–$C_{12}$ cycloalkoxy" refers to a $C_3$–$C_{12}$ cycloalkyl group attached to an oxygen atom. Typical $C_3$–$C_{12}$ cycloalkoxy groups include cyclopropyloxy, cyclobutyloxy, cyclopentyloxy, cyclohexyloxy and cycloheptyloxy and the like.

The term "$C_3$–$C_{12}$ cycloalkenyl" refers to a hydrocarbon ring structure having from three to twelve carbon atoms with at least one double bond. Typical $C_3$–$C_{12}$ cycloalkenyl groups include cyclopropenyl, cyclobutenyl, cyclopentenyl and the like.

The term "methyl($C_3$–$C_{12}$ cycloalkyl)" refers to a $C_3$–$C_{12}$ cycloalkyl group that is substituted with a methyl group. Typical methyl($C_3$–$C_{12}$ cycloalkyl) groups include 2-methylcycloproyl, 2-methylcyclobutyl, 3-methylcyclopentyl, 4-methylcyclohexyl and the like.

The term "$C_1$–$C_4$ alkylamino" refers to a straight or branched alkylamino chain having from one to four carbon atoms attached to a nitrogen atom. Typical $C_1$–$C_4$ alkylamino groups include methylamino, ethylamino, propylamino, isopropylamino, butylamino, sec-butylamino and the like.

The term "di($C_1$–$C_4$ alkyl)amino" refers to a di($C_1$–$C_4$ alkyl)amino chain having two straight or branched alkyl chains of from one to four carbon atoms attached to a common nitrogen atom. Typical di($C_1$–$C_4$ alkyl)amino groups include dimethylamino, diethylamino, ethylmethylamino, methylisopropyl-amino, dipropylamino, dibutylamino, methylbutylamino, t-butylisopropylamino, di-t-butylamino and the like.

The term "$C_2$–$C_{12}$ alkanoyl" represents a straight or branched chain alkyl chain having from one to four carbon atoms attached to a carbonyl moiety. Typical $C_2$–$C_{12}$ alkanoyl groups include ethanoyl, propanoyl, isopropanoyl, butanoyl, isobutanoyl, sec-butanoyl, t-butanoyl, pentanoyl and the like.

The term "$C_2$–$C_{12}$ alkanoylamino" represents a straight or branched chain alkyl group attached to a carbonylamino moiety. Typical $C_2$–$C_{12}$ alkanoylamino groups include ethanoylamino, propanoylamino, isopropanoylamino, butanoyl-amino, isobutanoylamino, sec-butanoylamino, t-butanoylamino, pentanoylamino and the like.

The terms "$C_7$–$C_{10}$ bicycloalkyl" represents two fused cycloalkyl rings having a total of seven to ten carbon atoms and "$C_7$–$C_{14}$ tricycloalkyl" represents three fused cycloalkyl rings having a total of seven to fourteen carbon atoms. Typical "$C_7$–$C_{10}$ bicycloalkyl" and "$C_7$–$C_{14}$ tricycloalkyl" groups include bicyclo[2.2.1.]hept-2-yl, bicyclo[2.2.1.]hept-4-en-2-yl, bicyclo[3.3.1.]non-3-yl, bicyclo[3.3.1.]non-2-yl, bicyclo[3.2.1.]oct-2-yl, bicyclo[2.2.2.]oct-2-yl, bicyclo[2.2.2]oct-5-en-2-yl, adamantyl and the like.

The term "hydroxy protecting group" refers to a substituent of an hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl) dimethylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy protecting group is trimethylsilyl. Further examples of hydroxy protecting groups are described in T. W. Greene, "Protective Groups in Organic Synthesis," John Wiley and Sons, New York, N.Y., (2nd ed., 1991) chapters 2 and 3. The term "protected hydroxy" refers to a hydroxy group bonded to one of the above hydroxy protecting groups.

The term "dideoxy" refers to compounds of the formula I where $R^{x1}$ and $R^{x2}$ are each hydrogen.

The term "inhibiting", i.e. a method of inhibiting parasitic or fungal activity, includes stopping, retarding or prophylactically hindering or preventing the growth or any attending characteristics and results from the existence of a parasite or fungus.

The term "contacting", i.e. contacting a compound of the invention with a parasite or fungus, includes a union or junction, or apparent touching or mutual tangency of a compound of the invention with a parasite or fungus. However, the term does not imply any further limitations to the process, such as by mechanism of inhibition, and the methods are defined to encompass the spirit of the invention, which is to inhibit parasitic and fungal activity by the action of the compounds and their inherent antiparasitic and antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napthhalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Typical examples of acyl groups at $R_2$ in formula I include benzoyl substituted by a polyoxa-alkyl group such as 2-methoxyethoxy (p is 0, m is 1), 2-ethoxyethoxy (p is 0, m is 2), 2-(2-ethoxyethoxy)ethoxy (m is 2, p is 1, n is 2), 3-(2-ethoxyethoxy)propoxy, 4-(2-methoxyethoxy) butoxy, and the like, or benzoyl substituted by alkynyl groups (—C≡C—($C_1$-$C_{12}$ alkyl)) such as propynyl, butynyl, hexynyl, undecynyl, and the like, or cis or trans alkenyl groups (—$CH_2$=$CH_2$—($C_1$-$C_{12}$ alkyl)) such as propenyl, butenyl, hexenyl, decenyl, and the like.

Examples of acyl groups where $R_2$ is a group of the formula

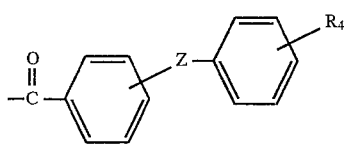

include diphenyl ethers (Z is —O—), diphenyl acetylenes (Z is —C≡C—), stilbenes (Z is —CH=CH—) and biphenyls (Z is a bond).

Examples of diphenyl ether groups include 4-(4-butoxyphenoxy)benzoyl, 4-(4-hexoxyphenoxy)benzoyl, 4-(4-ethoxyphenoxy)benzoyl, 4-(4-phenyloxyphenoxy) benzoyl, 4-[4- 4-(4-dodecyloxyphenoxy)benzoyl, 4-[4-(3-dimethylaminopropoxy)phenoxy]benzoyl and the like.

Examples of diphenyl acetylene and stilbene groups include 4-styrylbenzoyl, 4-(4-methoxystyryl)benzoyl, 4-(4-butoxystyryl)benzoyl, 4-(phenylethynyl)benzoyl, 4-(4-ethoxyphenylethynyl)benzoyl, 4-(4-cyclohexyloxyphenylethynyl)benzoyl and the like.

Examples of biphenyl groups include 4-[4-(butoxy) phenyl]benzoyl, 4-[4-(cyclobutylmethoxy)phenyl]benzoyl, 4-[4-cyclopentylmethoxy)phenyl]benzoyl, 4-[4-(cyclohexylethoxy)phenyl]benzoyl, 4-[4-(hexoxy)phenyl] benzoyl, 4-phenylbenzoyl, 4-[4-(11-amino-undecyloxy) phenyl]benzoyl, 4-[4-(11-formamidoundecyloxy)phenyl] benzoyl, 4-[4-(iso-pentoxy)phenyl]benzoyl and the like.

Examples of biphenyl groups where $R_4$ is —O—($CH_2$)$_r$—W—$R_5$ include 4-[4-[2-(N-cyclohexylpiperidino-4-yl) ethoxy]phenyl]benzoyl, 4-[4-[2-(N-hexylpiperidino-4-yl) ethoxy]phenyl ]benzoyl, 4-[4-[2-(4-benzylpiperidino)-ethoxy]phenyl]benzoyl, 4-[4-[2-(4-cyclohexylpiperidino)-ethoxy]phenyl]benzoyl and the like.

Examples of biphenyl and diphenyl ether groups where $R_4$ is -$Y^1$-$R_6$ include 4-[4-(phenylethynyl)phenyl]benzoyl, 4-[4-(phenylethynyl)phenoxy]benzoyl, 4-[4-(hexynyl) phenyl]benzoyl, 4-[4-(styryl)phenoxy ]benzoyl, 4-[4-[4-4-methylpiperidino)ethoxy]phenylethynyl]phenyl]benzoyl, and the like.

Acyl groups where $R_4$ is —O—($CH_2$)$_r$—W—$R_5$ may form acid addition salts of the basic amino groups of the piperidine and piperazine heterocyclic groups with organic or mineral acids such as hydrochloric acid, hydrobromic acid, sulfuric acid and phosphoric acid and with organic acids such as the sulfonic acids, benzenesulfonic acid, toluenesulfonic acid, methanesulfonic acid, acetic acid, chloroacetic acid, trifluoroacetic acid, benzoic acid, isophthalic acid, salicylic acid, citric acid, malic acid, succinic acid, malonic acid and the like.

Table 1, below, provides further examples of acyl groups, $R_2$, found on cyclic peptides of formula I.

TABLE 1

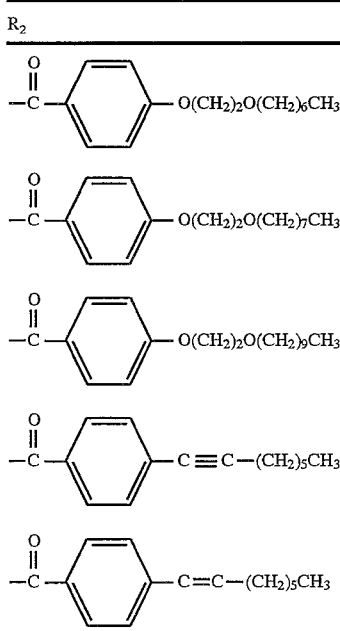

TABLE 1-continued
| $R_2$ |
|---|
| 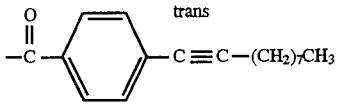 |
| 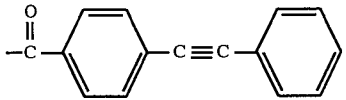 |
| 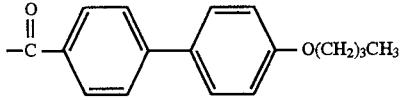 |
| 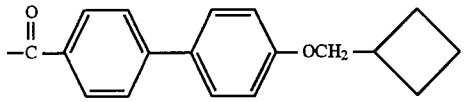 |
| 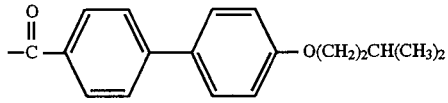 |
| 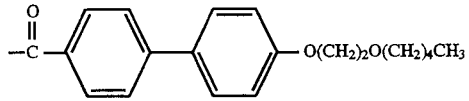 |
| 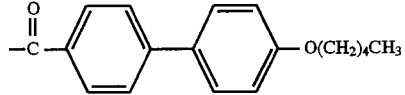 |
| 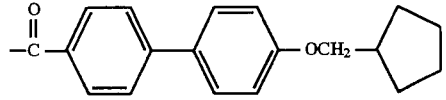 |
| 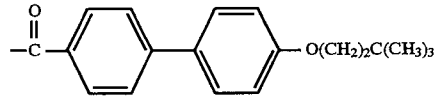 |
| 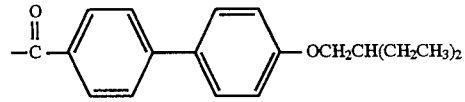 |
| 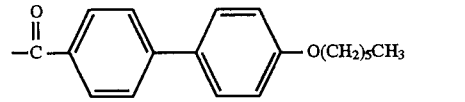 |
| 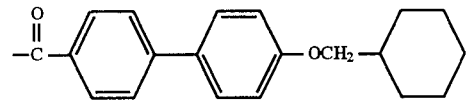 |
|  |
| 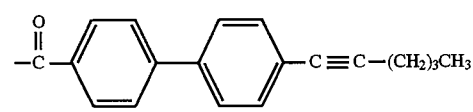 |

TABLE 1-continued
R₂
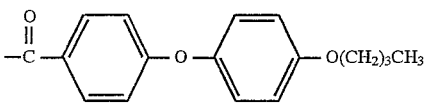
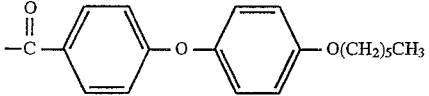
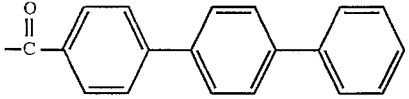
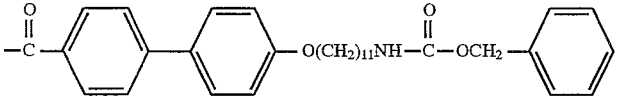
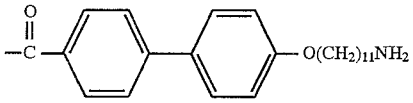
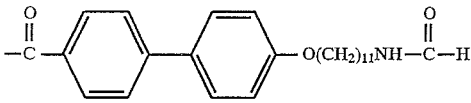
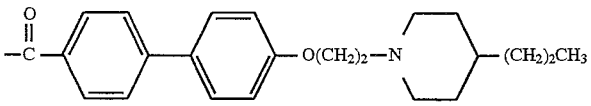
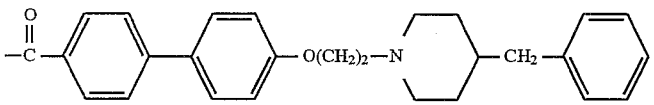
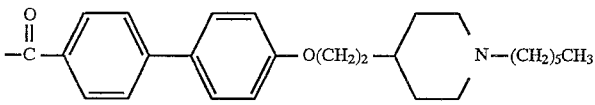
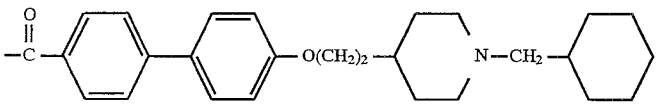
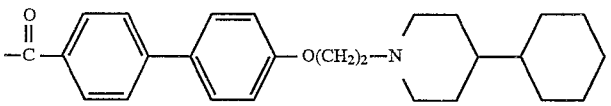
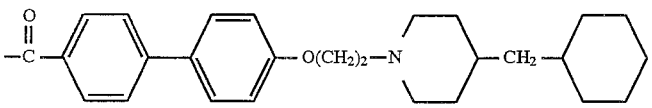
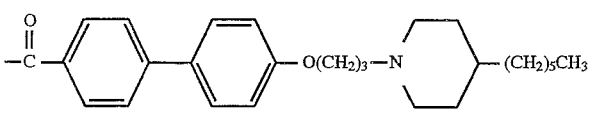
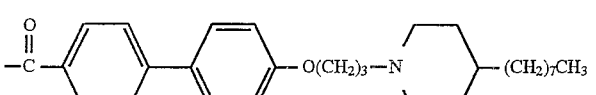

TABLE 1-continued

| $R_2$ |
|---|
| −C(=O)−C₆H₄−C₆H₄−O(CH₂)₃−N(piperidine)−(CH₂)₉CH₃ |
| −C(=O)−C₆H₄−O(CH₂)₂O(CH₂)₂OC₂H₅ |
| −C(=O)−C₆H₄−O(CH₂)₂OC₅H₁₁ |
| −C(=O)−C₆H₄−C≡C−C₅H₁₁ |
| −C(=O)−C₆H₄−C₆H₄−O(CH₂)₂N(CH₃)₂ |
| −C(=O)−C₆H₄−C₆H₄−O(CH₂)₂−N(piperidine) |
| −C(=O)−(CH₂)₄−O−C₆H₄−C₆H₅ |
| −C(=O)−(CH₂)₅−O−C₆H₄−C₆H₅ |
| −C(=O)−(CH₂)₁₀−O−C₆H₄−C₆H₅ |
| −C(=O)−CH(C₆H₅)−O−C₆H₄−C₆H₅ |
| −C(=O)−CH((CH₂)₃CH₃)−O−C₆H₄−C₆H₅ |
| −C(=O)−CH((CH₂)₅CH₃)−O−C₆H₄−C₆H₅ |
| −C(=O)−CH((CH₂)₁₁CH₃)−O−C₆H₄−C₆H₅ |

TABLE 1-continued

R₂

—C(=O)—[6-ethoxynaphthalen-1-yl]

—C(=O)—[3-hexyloxynaphthalen-2-yl]

—C(=O)—[3-octyloxynaphthalen-2-yl]

—C(=O)—[3-decyloxynaphthalen-2-yl]

—C(=O)—[6-(2-(4-cyclohexylmethylpiperidin-1-yl)ethoxy)naphthalen-2-yl]

—C(=O)—[6-hexyloxynaphthalen-2-yl]

—C(=O)—[6-octyloxynaphthalen-2-yl]

TABLE 1-continued

R$_2$

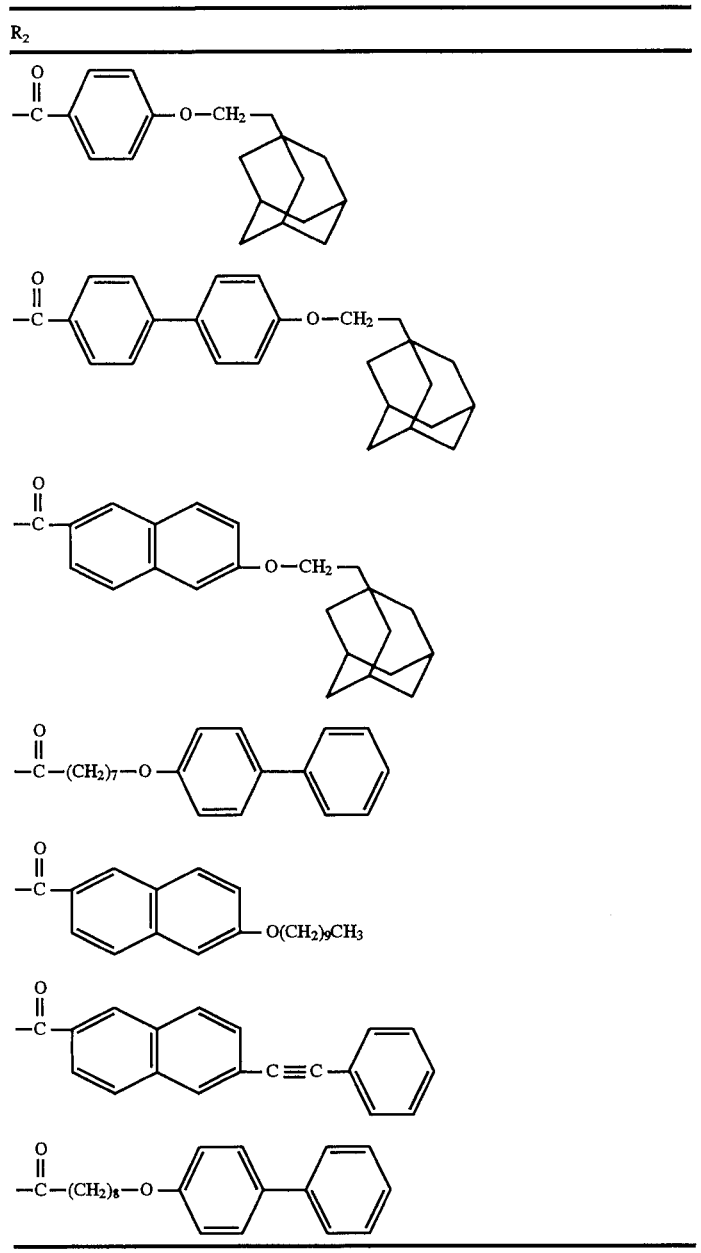

Preferred acyl groups, R$_2$, include groups of the formula:

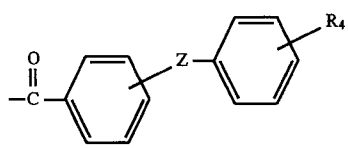

wherein:

Z is —C≡C—, —CH=CH—, —CH$_2$—CH$_2$—, or a bond;

A) R$_4$ is hydrogen, C$_1$–C$_{12}$ alkyl, C$_1$–C$_{12}$ substituted alkyl, C$_2$–C$_{12}$ alkenyl, C$_2$–C$_{12}$ substituted alkenyl, C$_2$–C$_{12}$ alkynyl, C$_2$–C$_{12}$ substituted alkynyl, C$_1$–C$_{12}$ alkoxy, C$_3$–C$_{12}$ cycloalkyl, C$_7$–C$_{10}$ bicycloalkyl, C$_7$–C$_{14}$ tricycloalkyl, C$_3$–C$_{12}$ cycloalkoxy, naphthyl, pyridyl, thienyl, benzothienyl, quinolyl or phenyl; or B) R$_4$ is phenyl substituted by amino, C$_1$–C$_{12}$ alkylthio, halo, C$_1$–C$_{12}$ alkyl, C$_2$–C$_{12}$ alkenyl, C$_2$–C$_{12}$ alkynyl, C$_1$–C$_{12}$ substituted alkyl, C$_2$–C$_{12}$ substituted alkenyl, C$_2$–C$_{12}$ substituted alkynyl, C$_1$–C$_{12}$ alkoxy, trifluoromethyl, phenyl, substituted phenyl, or a group of the formula —O—(CH$_2$)$_m$—[O—(CH$_2$)$_n$]$_p$—O—(C$_1$–C$_{12}$ alkyl) where m, n and p are as defined above; or C) R$_4$ is C$_1$–C$_{12}$ alkoxy substituted with halo, C$_3$–C$_{12}$ cycloalkyl, C$_7$–C$_{10}$ bicycloalkyl, C$_7$–C$_{14}$ tricycloalkyl, C$_1$–C$_6$ alkoxy, C$_2$–C$_{12}$ alkynyl, amino, C$_1$–C$_4$ alkylamino, di(C$_1$–C$_4$ alkyl)amino, formamido, C$_2$–C$_{12}$ alkanoylamino, or phenyl substituted with a group of the formula —O—(CH$_2$)$_m$—[O—(CH$_2$)$_n$]$_p$—O—(C$_1$–C$_{12}$ alkyl) where m, n and p are as defined above; or D) R$_4$ is —O—(CH$_2$)$_r$—W—R$_5$;

r is 2, 3 or 4;

W is pyrrolidino, piperidino or piperazino;

$R_5$ is hydrogen, $C_1-C_{12}$ alkyl, $C_3-C_{12}$ cycloalkyl, benzyl or $C_3-C_{12}$ cycloalkylmethyl; or E) $R_4$ is $-Y^1-R_6$;

$Y^1$ is $-C{\equiv}C-$ or $-CH{=}CH-$;

$R_6$ is $C_3-C_{12}$ cycloalkyl, $C_7-C_{10}$ bicycloalkyl, $C_7-C_{14}$ tricycloalkyl, $C_3-C_{12}$ cycloalkenyl, naphthyl, benzothiazolyl, thienyl, indanyl, fluorenyl, or phenyl substituted with $C_1-C_{12}$ alkylthio, $C_2-C_{12}$ alkenyl, $C_2-C_{12}$ alkynyl, halo($C_1-C_6$ alkoxy) or a group of the formula $-O-(CH_2)_r-W-R_5$ where r, W and $R_5$ are as defined above; or $R_6$ is phenyl substituted with a group of the formula $-O-(CH_2)_m-[O-(CH_2)_n]_p-O-(C_1-C_{12}$ alkyl) where m, n and p are as defined above; or F) $R_4$ is $C_1-C_{12}$ alkoxy substituted with a group of the formula $-NHC(O)R_7$;

$R_7$ is $C_1-C_6$ alkoxy, or phenyl($C_1-C_6$ alkoxy); or a pharmaceutically acceptable salt thereof.

More preferred are acyl groups, $R_2$, of the formula:

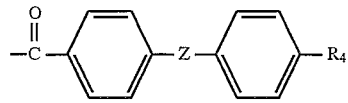

where Z is $-C{\equiv}C-$ or a bond;

or a pharmaceutically acceptable salt thereof.

Table 2, below, provides a list of preferred acyl groups, $R_2$, found on cyclic peptides of formula I.

TABLE 2

$R_2$

- $-C(O)-C_6H_4-C_6H_4-C{\equiv}C-C_6H_4-O(CH_2)_2CH_3$
- $-C(O)-C_6H_4-C_6H_4-C{\equiv}C-C_6H_4-O(CH_2)_2OC(CH_3)_3$
- $-C(O)-C_6H_4-C_6H_4-C{\equiv}C-C_6H_4-O(CH_2)_2O(CH_2)_3CH_3$
- $-C(O)-C_6H_4-C{\equiv}C-C_6H_4-C_6H_4-O(CH_2)_2CH_3$
- $-C(O)-C_6H_4-C{\equiv}C-C_6H_4-C_6H_4-O(CH_2)_2O(CH_2)_3CH_3$
- $-C(O)-C_6H_4-C{\equiv}C-C_6H_4-C_6H_4-O(CH_2)_2OC(CH_3)_3$
- $-C(O)-C_6H_4-C_6H_4-C_6H_4-O(CH_2)_3CH_3$
- $-C(O)-C_6H_4-C_6H_4-C_6H_4-O(CH_2)_4CH_3$
- $-C(O)-C_6H_4-C_6H_4-C_6H_4-O(CH_2)_5CH_3$
- $-C(O)-C_6H_4-C_6H_4-C_6H_4-O(CH_2)_2O(CH_2)_3CH_3$

TABLE 2-continued

| $R_2$ |
|---|

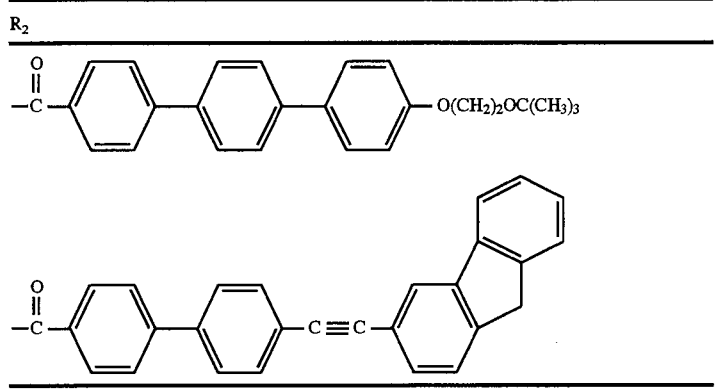

Preferred compounds of this invention are those compounds of formula I where:

R', R", and R'" are each methyl;
$R^{y1}$, $R^{y2}$, $R^{y3}$, $R^{y4}$ are each hydroxy;
or a pharmaceutically acceptable salt thereof.

Of these compounds, more preferred are those compounds of formula I where:

$R^{x1}$ and $R^{x2}$ are hydrogen;

or a pharmaceutically acceptable salt thereof.

The compounds of formula I may be prepared according to Reaction Scheme I, as follows.

Reaction Scheme I

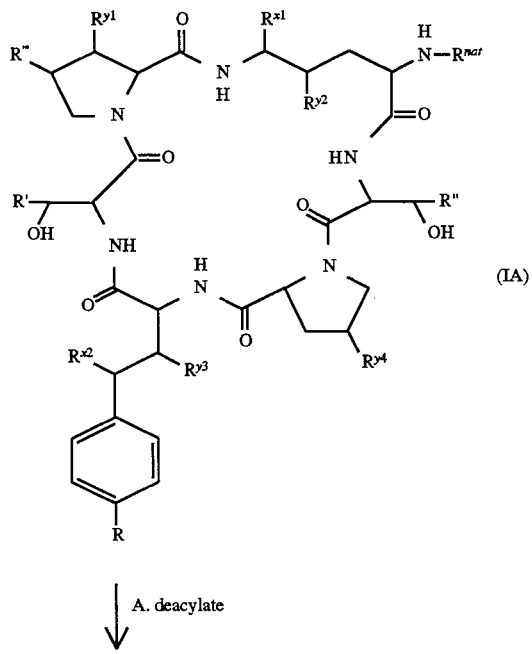

-continued
Reaction Scheme I
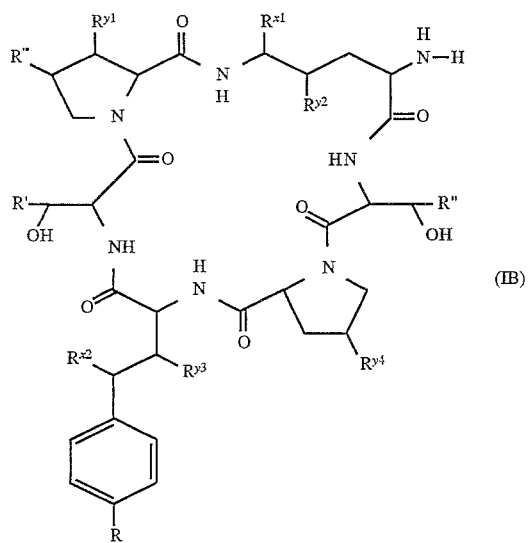
(IB)
↓ B. re-acylate
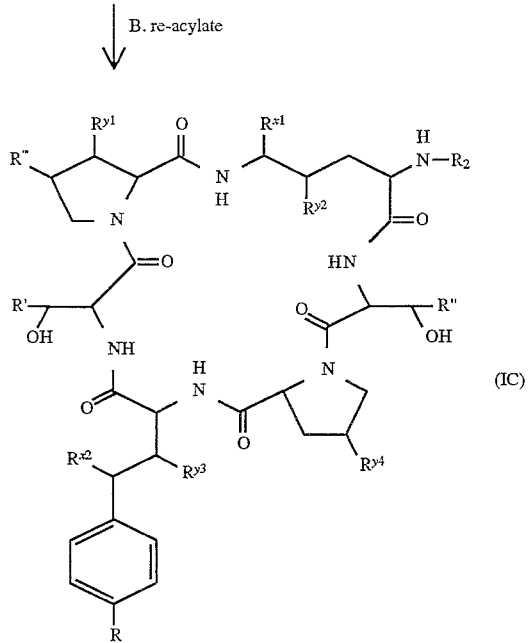
(IC)

-continued
Reaction Scheme I

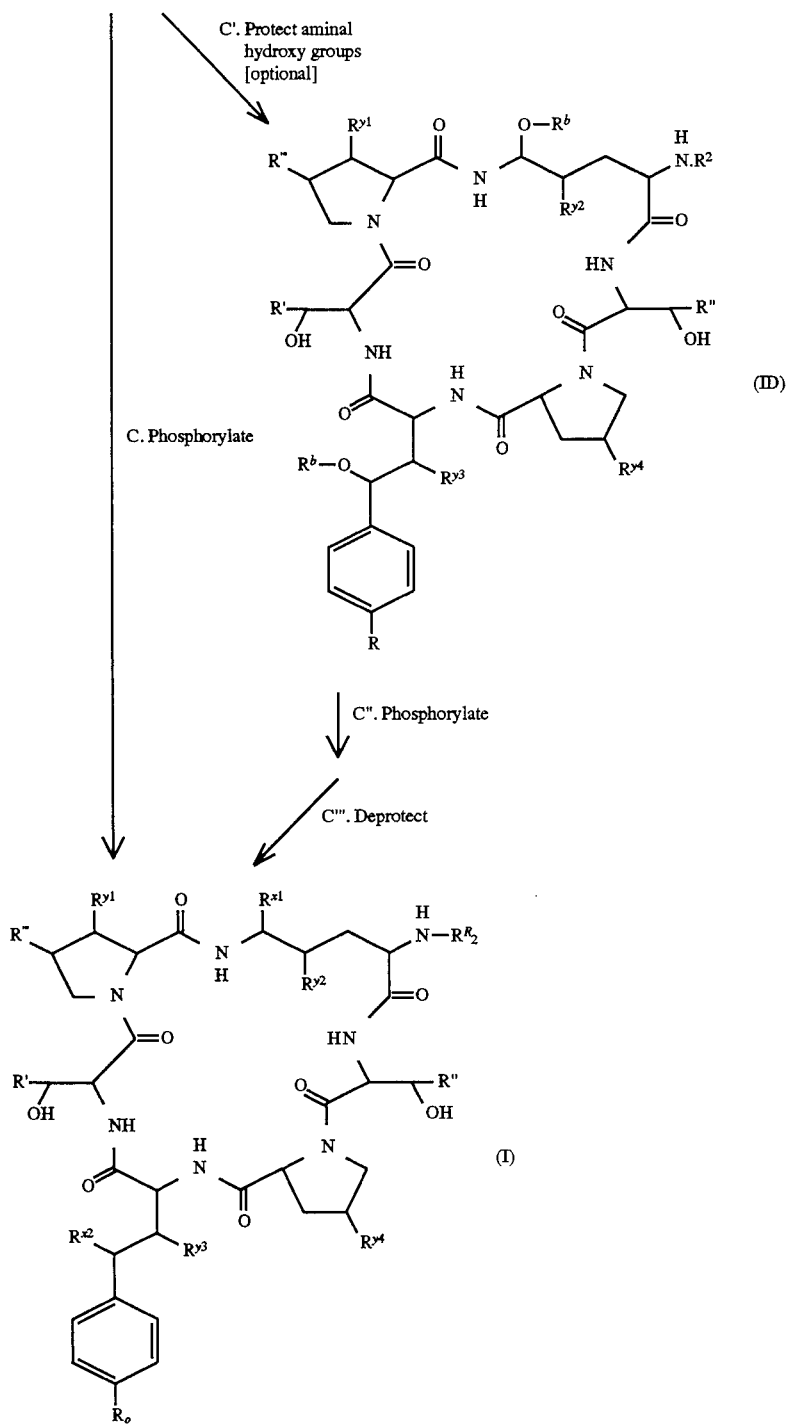

wherein:

$R^{nat}$ is a naturally occurring cyclic peptide sidechain;

R is hydroxy;

$R^b$ is an hydroxy protecting group; and

R', R", R'", $R^{x1}$, $R^{x2}$, $R^{y1}$, $R^{y2}$, $R^{y3}$, $R^{y4}$, R, $R_0$ and $R_2$ are as defined above.

Reaction scheme I, above, is accomplished by carrying out reactions A-C (or A-C'"), in order. Once a reaction is complete, the intermediate compound may be isolated by procedures well-known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel, alumina and the like, before carrying out the next step of the reaction scheme.

In reaction IA, a naturally occurring cyclic peptide of the formula (IA) is deacylated using procedures known in the art to provide an amino nucleus of formula (IB). This reaction is typically carried out using enzymatic acylation by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304,716, herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched $C_{15}$ side chain), L-671,329 ($C_{16}$ branched side chain), S 31794/F1 (tetradecanoyl side chain), sporiofungin ($C_{15}$ branched side chain), $FR_{901379}$ (palmitoyl side chain) and the like. A preferred naturally occurring cyclic peptide is echinocandin B (a compound of formula (IA) where R', R", and R'" are each methyl, $R^{x1}$ and $R^{x2}$ are each hydroxy, $R^{y1}$, $R^{y2}$, $R^{y3}$, $R^{y4}$ are each hydroxy, R is hydroxy and $R_2$ is linoleoyl).

In Reaction IB, the resulting amino nucleus is then re-acylated using procedures known in the art to provide a compound of formula I where $R_2$ is an acyl group as defined hereinabove.

For example, the amino nucleus may be acylated by reaction with an appropriately substituted acyl halide, preferably in the presence of an acid scavenger such as a tertiary amine, such as triethylamine. The reaction is typically carried out at a temperature of from about −20° C. to about 25° C. Typical solvents for this reaction include polar aprotic solvents such as dioxane or dimethylformamide. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include dicyclohexylcarbodiimide (DCC), N,N'-carbonyldiimidazole, bis(2-oxo-3-oxazolidinyl)phosphinic chloride (BOP—Cl), N-ethoxycarbonyl-2-ethoxy-1,2-dihydroquinoline (EEDQ), benzotriazol-1-yloxytripyrrolidinophosphonium hexafluorophosphate (PyBOP) and the like.

In addition, the amino nucleus may be acylated with an activated ester of a carboxylic acid (RCOOH) such as an ester of a carboxylic acid of the formula $R_2$-COOH and p-nitrophenyl, 2,4,5-trichlorophenyl, hydroxybenzotriazole hydrate ($HOBT.H_2O$), pentafluorophenol, N-hydroxysuccinimide and the like. Preferred acylating moieties are the active esters of the carboxylic acid $R_2$—COOH such as 2,4,5-trichlorophenyl ester and HOBT ester. The reaction is typically carried out for one to sixty five hours at a temperature from about 0° C. to about 30° C. in an aprotic solvent. The reaction is generally complete after about twenty four to forty eight hours when carried out a temperature of from about 15° C. to about 30° C. Typical solvents for this reaction are tetrahydrofuran and dimethylformamide or a mixture of such solvents. The amino nucleus is generally employed in equimolar proportions relative to the activated ester or with a slight excess of the amino nucleus.

In Reaction IC, the compound of formula (IC) is phosphorylated by reaction with an appropriately substituted alkyl or phenyl phosphate to provide a compound of formula I where $R_0$ is $P(O)_2OH$—$R_1$ where $R_1$ is $C_1$–$C_6$ alkoxy or phenoxy, or by reaction with an appropriately substituted alkyl or phenyl phosphonic acid to provide a compound of formula I where $R_0$ is —$P(O)_2OH$—$R_1$ where $R_1$ is $C_1$–$C_6$ alkyl, an appropriately substituted phenyl or benzyl moiety. The reaction is carried out in the presence of a base such as lithium trimethylsilanolate (LiOTMS), lithium bis (trimethylsilyl)amide (LHMDS), pyridine and the like. The reaction is typically carried out for up to one hour at a temperature from about −30° C. to about 0° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base. Phosphorylation of an amino nucleus with unprotected aminal hydroxy groups ($R^{x1}$ and $R^{x2}$) is typically carried out at a temperature from about −30° C. to about −15° C.

Alternatively, in Reaction IC' the acylated nucleus of formula (IC), where $R^{x1}$ and/or $R^{x2}$ are hydroxy, may be optionally protected with an hydroxy protecting group using procedures known in the art. For example, the reaction is typically carried out by combining the compound of formula (IC) with a suitable hydroxy protecting group in the presence of a catalyst at a temperature in the range of from about 0° C. to about 40° C. for about one to five hours in a mutual inert solvent. The hydroxy protecting group is generally employed in an amount ranging from about equimolar proportions to about a 100 molar excess relative to the compound of formula (IC), preferably in a large molar excess. Suitable catalysts include strong acids such as p-toluenesulfonic acid, camphorsulfonic acid (CSA), hydrochloric acid, sulfuric acid, trifluoroacetic acid and the like. Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about 2 to 4 hours. It is not necessary to protect the dideoxy compounds of formula (IC), that is, those compounds of formula (IC) where $R^{x1}$ and $R^{x2}$ are hydrogen.

Reaction IC" is carried out as described above in Reaction IC, above.

In Reaction IC"', the hydroxy protecting groups that were used to protect the aminal hydroxy moieties in Reaction IC', above, are removed according to procedures known in the art to provide the desired compound of formula I. For example, the protecting groups can be removed by reaction with a Lewis acid in a mutual inert organic solvent such as methylene chloride. Examples of Lewis acids include trimethylsilylbromide, boron trifluoride etherate and the like. The reaction is typically carried out at a temperature of from about 0° C. to about 40° C., preferably at a temperature of from about 20° C. to about 30° C. A preferred Lewis acid is boron trifluoride etherate.

The cyclic peptides used to make the compounds of the present invention may be prepared by fermentation of known microorganisms. For example, the cyclic peptide of formula (IB) where R', R", and R'" are methyl, $R^{x1}$ and $R^{x2}$ are hydroxy, $R^{y1}$, $R^{y2}$, $R^{y3}$, $R^{y4}$ are hydroxy, and R is hydroxy (cyclic nucleus corresponding to A-30912A) may be prepared using the procedure detailed in Abbott et al., U.S. Pat. No. 4,293,482, which is herein incorporated by reference. The cyclic peptide of formula (IB) where R', R", and R''' are methyl, $R^{x1}$ is hydroxy, $R^{x2}$ is hydrogen, $R^{y1}$, $R^{y2}$, $R^{y3}$, $R^{y4}$ are hydroxy and R is hydroxy (cyclic nucleus corresponding to A-30912B) may be prepared using the procedure detailed in Abbott et al., U.S. Pat. No. 4,299,763, which is herein incorporated by reference. The cyclic peptide of formula (IB) where R', R", and R'" are methyl, $R^{x1}$ and $R^{x2}$ are hydrogen, $R^{y1}$, $R^{y3}$ and $R^{y4}$ are hydroxy, $R^{y2}$ is hydrogen and R is hydroxy (cyclic nucleus corresponding to A-30912D) may be prepared using the procedure detailed in Abbott et al., U.S. Pat. No. 4,299,762, which is herein incorporated by reference. Aculeacin may be prepared using the procedure detailed in Mizuno et al., U.S. Pat. No. 3,978,210 which is herein incorporated by reference. The cyclic peptide of formula (IB) where R' is —$CH_2C(O)NH_2$, R" is methyl, R'" is hydrogen, $R^{x1}$, $R^{x2}$, $R^{y1}$, $R^{y3}$, $R^4$ are hydroxy, R is hydroxy may be prepared by deacylating the cyclic peptide prepared using the procedure detailed in Shieh-Shung et al., U.S. Pat. No. 5,198,421, which is herein incorporated by reference.

The dideoxy compounds of formula I are prepared by removing the benzylic and aminal hydroxy groups ($R^{x2}$ and $R^{x1}$, respectively). The hydroxy groups may be removed by subjecting a non-dideoxy compound of formula I (where $R_2$ is hydrogen or acyl) to a strong acid and a reducing agent at a temperature of between –5° C. and 70° C., in a suitable solvent. Typical strong acids include trichloroacetic acid, trifluoroacetic acid or borontrifluoride etherate. A preferred strong acid is trifluoroacetic acid. Typical reducing agents include sodium cyanoborohydride or triethylsilane. A preferred reducing agent is triethylsilane. Suitable solvents include methylene chloride, chloroform or acetic acid, preferably methylene chloride. The strong acid should be present in an amount of from 2 to 60 mol per mol of substrate, and the reducing agent should be present in an amount of 2 to 60 mol per mol of substrate. This process affords selective removal of the aminal and benzylic hydroxy groups.

The $R_2$—COOH precursor acids are prepared by hydrolyzing a nitrile of the formula $R_2$—CN or an ester of the formula $R_2$—COO($C_1$–$C_4$ alkyl). The nitrile and ester intermediates may be prepared using procedures known in the art.

For example, the nitrile and ester intermediates where $R_2$ is an alkoxy aryl moiety may be prepared using Procedure A or Procedure B, described below.

Procedure A

One equivalent of an alkyl bromide, iodide, or p-toluenesulfonate is added to a mixture containing one equivalent of a base, such as potassium t-butoxide or potassium carbonate, and one equivalent of an hydroxy aryl compound in 200–300 ml of acetonitrile. The resulting reaction mixture is refluxed for approximately six hours and then concentrated in vacuo to provide a residue. This residue is dissolved in a mixture of diethyl ether and a 2N sodium hydroxide solution. The resulting layers are separated and the organic layer is dried over magnesium sulfate, filtered and dried to provide the desired alkoxy aryl product.

Procedure B

One equivalent of diethylazodicarboxylate is added dropwise over ten minutes, at room temperature, to a mixture containing one equivalent of an hydroxy aryl compound, one equivalent of an alkyl alcohol and one equivalent of triphenylphosphine in 200–300 ml of tetrahydrofuran. After approximately seventeen hours, the solvent is removed in vacuo to provide a residue. This residue is dissolved in diethyl ether and the resulting mixture is washed with a 2N sodium hydroxide solution, dried over magnesium sulfate, filtered and concentrated to provide a product which is then crystallized from a diethyl ether/pentane mixture or, if the product contains a tertiary amine, the hydrochloride salt is formed and crystallized from a methanol/ethyl acetate mixture.

The nitrile and ester intermediates where $R_2$ is an alkynyl or alkenyl aryl moiety may be prepared using Procedure C, below.

Procedure C

A mixture containing two equivalents of triethylamine, 0.05 equivalent of palladium dichloride, 0.1 equivalent of triphenylphosphine, 0.025 equivalent of cuprous iodide and one equivalent of an alkyne or two equivalents of an alkene, is added to one equivalent of an aryl bromide, iodide, or trifluoromethanesulfonate in acetonitrile (600 ml/0.1 mol of aryl reactant), under nitrogen. The resulting mixture is refluxed for approximately seventeen hours and then the solvent is removed in vacuo to provide a residue. This residue is slurried in 300 ml of diethyl ether and then filtered to remove the resultant solids. The filtrate is washed with a 1N hydrochloric acid solution, dried over magnesium sulfate, filtered and then dried to provide the desired product.

The ester intermediates where $R_2$ is a terphenyl moiety may be prepared using Procedure D, below.

Procedure D

1. Formation of boronic acid reactant

Butyl lithium (1.2 equivalents) is added to one equivalent of a cold (–78° C.) aryl halide in tetrahydrofuran. After approximately fifteen minutes, two equivalents of triisopropyl borate are added. After approximately ten minutes, the reaction mixture is warmed to room temperature, and then quenched by the addition of water, followed by the addition of a 1N hydrochloric acid solution. The resulting layers are separated and the organic layer is concentrated in vacuo to provide a solid. This solid is collected by filtration and then washed with hexane to provide a pure boronic acid product.

2. Formation of terphenyl ester

Tetrakis(triphenylphosphine)palladium (0.03 equivalent) is added to a mixture containing one equivalent of an aryl boronic acid, 1.5 equivalents of potassium carbonate and one equivalent of methyl 4-iodobenzoate (or trichlorophenyl ester of iodobenzoate) in nitrogen-purged toluene. The resulting reaction mixture is refluxed for approximately seven hours and then decanted to remove the potassium carbonate and dried in vacuo to provide a residue. This residue is triturated in acetonitrile and then filtered to provide the desired solid product.

The aryl nitriles and esters described above may be converted to the corresponding carboxylic acids by hydrolysis using Procedure E or Procedure F, below.

Procedure E

An aryl nitrile is dissolved in ethanol and an excess of 50% sodium hydroxide solution and refluxed for approximately two hours. Water is added to the resulting reaction mixture until a solid precipitates. This solid is collected by filtration, added to a dioxane/6N hydrochloric acid mixture and the resulting mixture is refluxed for approximately seventeen hours. When the reaction is substantially complete, the carboxylic acid product is crystallized by the addition of water and then collected by filtration and dried in vacuo.

Procedure F

An excess of a 2N sodium hydroxide solution is added to an aryl ester in methanol, and the resulting solution is refluxed for approximately five hours and then acidified by the addition of excess hydrochloric acid. Water is added to the resulting reaction mixture until a solid (carboxylic acid) precipitates. The carboxylic acid is collected by filtration and dried in vacuo.

The carboxylic acids may be converted to the corresponding 2,4,5-trichlorophenyl esters using Procedure G, below. These activated esters are then used to acylate the amino nucleus, as described above in Reaction Scheme IC.

Procedure G

A mixture containing one equivalent of an aryl carboxylic acid, one equivalent of 2,4,5-trichlorophenol, and one equivalent of N,N'-dicyclohexylcarbodiimide (DCC) in methylene chloride is stirred for approximately seventeen hours and then filtered. The filtrate is concentrated to provide a residue. This residue is dissolved in diethyl ether, filtered, and pentane is added until crystallization begins. The crystalline product is collected by filtration and dried in vacuo.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The nuclear magnetic resonance spectra were obtained on a General Electric QE-300 300 MHz instrument. The chemical shifts are expressed in delta ($\delta$) values (parts per million downfield from tetramethylsilane).

Preparation 1

The following nitrile and ester intermediates where $R_2$ is an alkoxy aryl moiety were prepared substantially in accordance with Procedure A, detailed above.

TABLE A

| Alkyl halide or tosylate | mass (g) | Alkoxy aryl product | mass (g) |
|---|---|---|---|
| I—(CH$_2$)$_3$CH$_3$ | 9.4 | CH$_3$(CH$_2$)$_3$O—C$_6$H$_4$—C$_6$H$_4$—CN | 3.2 |
| 4-CH$_3$-C$_6$H$_4$-SO$_3$—CH$_2$-cyclobutyl | 12.3 | cyclobutyl-CH$_2$O—C$_6$H$_4$—C$_6$H$_4$—CN | 5.3 |
| Br—(CH$_2$)$_2$CH(CH$_3$)$_2$ | 7.7 | (CH$_3$)$_2$CH(CH$_2$)$_2$O—C$_6$H$_4$—C$_6$H$_4$—CN | 9.2 |
| 4-CH$_3$-C$_6$H$_4$-SO$_3$—(CH$_2$)$_2$O(CH$_2$)$_4$CH$_3$ | 7.6 | CH$_3$(CH$_2$)$_4$O—(CH$_2$)$_2$O—C$_6$H$_4$—C$_6$H$_4$—CN | 4.8 |
| Br—(CH$_2$)$_4$CH$_3$ | 15.3 | CH$_3$(CH$_2$)$_4$O—C$_6$H$_4$—C$_6$H$_4$—CN | 20.3 |
| 4-CH$_3$-C$_6$H$_4$-SO$_3$—CH$_2$-cyclopentyl | 13.0 | cyclopentyl-CH$_2$O—C$_6$H$_4$—C$_6$H$_4$—CN | 12.2 |
| 4-CH$_3$-C$_6$H$_4$-SO$_3$—(CH$_2$)$_2$C(CH$_3$)$_3$ | 13.1 | (CH$_3$)$_3$C(CH$_2$)$_2$O—C$_6$H$_4$—C$_6$H$_4$—CN | 11.8 |
| Br—CH$_2$CH(CH$_2$CH$_3$)$_2$ | 8.5 | (CH$_2$CH$_3$)$_2$CHCH$_2$O—C$_6$H$_4$—C$_6$H$_4$—CN | 3.0 |
| I—(CH$_2$)$_5$CH$_3$ | 10.8 | CH$_3$(CH$_2$)$_5$O—C$_6$H$_4$—C$_6$H$_4$—CN | 11.4 |

TABLE A-continued

| Alkyl halide or tosylate | mass (g) | Alkoxy aryl product | mass (g) |
|---|---|---|---|
| Br—(CH$_2$)$_2$—cyclohexyl | 4.2 | cyclohexyl-(CH$_2$)$_2$O—C$_6$H$_4$—C$_6$H$_4$—CO$_2$CH$_3$ | 4.5 |
| CH$_3$-C$_6$H$_4$-SO$_3$—(CH$_2$)$_2$O(CH$_2$)$_6$CH$_3$ | 23.4 | CH$_3$(CH$_2$)$_6$O—(CH$_2$)$_2$O—C$_6$H$_4$—CO$_2$CH$_2$CH$_3$ | 20.9 |
| CH$_3$-C$_6$H$_4$-SO$_3$—(CH$_2$)$_2$O(CH$_2$)$_7$CH$_3$ | 25.8 | CH$_3$(CH$_2$)$_7$O—(CH$_2$)$_2$O—C$_6$H$_4$—CO$_2$CH$_2$CH$_3$ | 7.9 |
| CH$_3$-C$_6$H$_4$-SO$_3$—(CH$_2$)$_2$O(CH$_2$)$_9$CH$_3$ | 27.1 | CH$_3$(CH$_2$)$_9$O—(CH$_2$)$_2$O—C$_6$H$_4$—CO$_2$CH$_2$CH$_3$ | 21.0 |
| I—(CH$_2$)$_3$CH$_3$ | 6.1 | CH$_3$(CH$_2$)$_3$O—C$_6$H$_4$—O—C$_6$H$_4$—CO$_2$CH$_3$ | 12.3 |
| I—(CH$_2$)$_5$CH$_3$ | 4.3 | CH$_3$(CH$_2$)$_5$O—C$_6$H$_4$—O—C$_6$H$_4$—CO$_2$CH$_3$ | 4.7 |
| I—(CH$_2$)$_2$CH$_3$ | 2.6 | CH$_3$(CH$_2$)$_2$O—C$_6$H$_4$—C$_6$H$_4$—C≡C—C$_6$H$_4$—CO$_2$CH$_3$ | 4.4 |
| CH$_3$-C$_6$H$_4$-SO$_3$—(CH$_2$)$_2$O(CH$_2$)$_3$CH$_3$ | 2.7 | CH$_3$(CH$_2$)$_3$O—(CH$_2$)$_2$O—C$_6$H$_4$—C$_6$H$_4$—C≡C—C$_6$H$_4$—CO$_2$CH$_3$ | 2.6 |
| CH$_3$-C$_6$H$_4$-SO$_3$—(CH$_2$)$_2$OC(CH$_3$)$_3$ | 2.7 | (CH$_3$)$_3$CO—(CH$_2$)$_2$O—C$_6$H$_4$—C$_6$H$_4$—C≡C—C$_6$H$_4$—CO$_2$CH$_3$ | 2.6 |

TABLE A-continued

| Alkyl halide or tosylate | mass (g) | Alkoxy aryl product | mass (g) |
|---|---|---|---|
| I—(CH$_2$)$_2$CH$_3$ | 3.8 | CH$_3$(CH$_2$)$_2$O—[C$_6$H$_4$]—C≡C—[C$_6$H$_4$]—CO$_2$CH$_3$ | 1.4 |
| 4-CH$_3$-C$_6$H$_4$-SO$_3$—(CH$_2$)$_3$O(CH$_2$)$_3$CH$_3$ | 3.6 | CH$_3$(CH$_2$)$_3$O—(CH$_2$)$_2$O—[C$_6$H$_4$]—C≡C—[C$_6$H$_4$]—CO$_2$CH$_3$ | 5.1 |
| 4-CH$_3$-C$_6$H$_4$-SO$_3$—(CH$_2$)$_2$OC(CH$_3$)$_3$ | 4.9 | (CH$_3$)$_3$CO—(CH$_2$)$_2$O—[C$_6$H$_4$]—C≡C—[C$_6$H$_4$]—[C$_6$H$_4$]—CO$_2$CH$_3$ | 5.2 |

Preparation 2

The following nitrile and ester intermediates where $R_2$ is an alkoxy aryl moiety were prepared substantially in accordance with Procedure B, detailed above.

TABLE B

| Alkyl alcohol | mass (g) | Alkoxy Aryl Product | mass (g) |
|---|---|---|---|
| HO—(CH$_2$)$_2$—N(piperidine)—(CH$_2$)$_2$CH$_3$ | 3.6 | CH$_3$(CH$_2$)$_2$—N(piperidine)—(CH$_2$)$_2$O—[biphenyl]—CO$_2$CH$_3$ | 6.2 |
| HO—(CH$_2$)$_2$—N(piperidine)—CH$_2$—Ph | 6.1 | Ph—CH$_2$—N(piperidine)—(CH$_2$)$_2$O—[biphenyl]—CO$_2$CH$_3$ | 4.3 |
| HO—(CH$_2$)$_2$—N—(CH$_2$)$_5$CH$_3$ | 0.5 | CH$_3$(CH$_2$)$_5$—N—(CH$_2$)$_2$O—[biphenyl]—CO$_2$CH$_3$ | 0.8 |
| HO—(CH$_2$)$_2$—N(piperidine)—CH$_2$—Cy | 0.5 | Cy—CH$_2$—N(piperidine)—(CH$_2$)$_2$O—[biphenyl]—CO$_2$CH$_3$ | 0.5 |
| HO—(CH$_2$)$_2$—N(piperidine)—Cy | 2.3 | Cy—N(piperidine)—(CH$_2$)$_2$O—[biphenyl]—CO$_2$CH$_3$ | 1.3 |
| HO—(CH$_2$)$_2$—N(piperidine)—CH$_2$—Cy | 9.3 | Cy—CH$_2$—N(piperidine)—(CH$_2$)$_2$O—[biphenyl]—CO$_2$CH$_3$ | 9.6 |
| HO—CH$_2$—[C$_6$H$_4$]—(CH$_2$)$_3$CH$_3$ | 10.0 | CH$_3$(CH$_2$)$_3$—[C$_6$H$_4$]—CH$_2$O—[C$_6$H$_4$]—CO$_2$CH$_2$CH$_3$ | 13.6 |

Preparation 3

The following ester intermediates where $R_2$ is an alkynyl or alkenyl aryl moiety were prepared substantially in accordance with Procedure C, detailed above.

TABLE C

| Alkene or alkyne | mass (g) | Aryl halide | mass (g) | Alkenyl or alkynl aryl product | mass (g) |
|---|---|---|---|---|---|
| HC≡C—(CH$_2$)$_5$CH$_3$ | 12.1 | 4-I-C$_6$H$_4$-CO$_2$CH$_3$ | 28.8 | CH$_3$(CH$_2$)$_5$—C≡C—C$_6$H$_4$-4-CO$_2$CH$_3$ | 26.2 |
| HC≡C—(CH$_2$)$_5$CH$_3$ | 6.1 | 4-I-C$_6$H$_4$-CO$_2$CH$_3$ | 14.4 | CH$_3$(CH$_2$)$_5$—CH=CH—C$_6$H$_4$-4-CO$_2$CH$_3$ (trans) | 0.6 |
| HC≡C—(CH$_2$)$_7$CH$_3$ | 15.2 | 4-I-C$_6$H$_4$-CO$_2$CH$_3$ | 28.8 | CH$_3$(CH$_2$)$_7$—C≡C—C$_6$H$_4$-4-CO$_2$CH$_3$ | 28.1 |
| HC≡C—C$_6$H$_5$ | 1.9 | 4-I-C$_6$H$_4$-CO$_2$CH$_3$ | 5.1 | C$_6$H$_5$—C≡C—C$_6$H$_4$-4-CO$_2$CH$_3$ | 1.9 |
| HC≡C—Si(CH$_3$)$_3$ | 4.3 | 4-I-C$_6$H$_4$-CO$_2$CH$_3$ | 11.5 | (CH$_3$)$_3$Si—C≡C—C$_6$H$_4$-4-CO$_2$CH$_3$ | 11.2 |
| HC≡C—C$_6$H$_5$ | 1.8 | 4-I-C$_6$H$_4$-C$_6$H$_4$-4-CO$_2$CH$_3$ | 6.0 | C$_6$H$_5$—C≡C—C$_6$H$_4$-C$_6$H$_4$-4-CO$_2$CH$_3$ | 2.6 |
| HC≡C—(CH$_2$)$_3$CH$_3$ | 1.4 | 4-I-C$_6$H$_4$-C$_6$H$_4$-4-CO$_2$CH$_3$ | 6.0 | CH$_3$(CH$_2$)$_3$—C≡C—C$_6$H$_4$-C$_6$H$_4$-4-CO$_2$CH$_3$ | 5.1 |
| HC≡C—Si(CH$_3$)$_3$ | 10.9 | 4-I-C$_6$H$_4$-C$_6$H$_4$-4-CO$_2$CH$_3$ | 40.0 | (CH$_3$)$_3$Si—C≡C—C$_6$H$_4$-C$_6$H$_4$-4-CO$_2$CH$_3$ | 23.3 |
| HC≡C—(CH$_2$)$_7$CH$_3$ | 7.6 | 5-Br-furan-2-CO$_2$CH$_3$ | 11.3 | CH$_3$(CH$_2$)$_7$—C≡C-(furan-2)-CO$_2$CH$_3$ | 11.4 |

TABLE C-continued

| Alkene or alkyne | mass (g) | Aryl halide | mass (g) | Alkenyl or alkynl aryl product | mass (g) |
|---|---|---|---|---|---|
| HC≡C–C₆H₄–C₆H₄–CO₂CH₃ | 9.7 | I–C₆H₄–OH | 10.5 | HO–C₆H₄–C≡C–C₆H₄–C₆H₄–CO₂CH₃ | 10.2 |
| HC≡C–C₆H₄–CO₂CH₃ | 34.4 | Br–C₆H₄–C₆H₄–OH | 22.2 | HO–C₆H₄–C₆H₄–C≡C–C₆H₄–CO₂CH₃ | 19.4 |
| HC≡C–C₆H₄–C₆H₄–CO₂CH₃ | 1.2 | 2-bromofluorene | 1.2 | fluorenyl–C≡C–C₆H₄–C₆H₄–CO₂CH₃ | 1.5 |

Preparation 4

The following ester intermediates where $R_2$ is a terphenyl moiety were prepared substantially in accordance with Procedure D, detailed above.

TABLE D.1

| Aryl halide (R$^D$ is bromide) | mass (g) | Boronic acid reactant (R$^D$ is B(OH)$_2$ mass (g) |
|---|---|---|
| R$^D$—⟨phenyl⟩—⟨phenyl⟩—O(CH$_2$)$_3$CH$_3$ | 10.6 | 6.1 |
| R$^D$—⟨phenyl⟩—⟨phenyl⟩—O(CH$_2$)$_4$CH$_3$ | 31.0 | 12.0 |
| R$^D$—⟨phenyl⟩—⟨phenyl⟩—O(CH$_2$)$_5$CH$_3$ | 10.9 | 4.1 |
| R$^D$—⟨phenyl⟩—⟨phenyl⟩—O(CH$_2$)$_2$—O(CH$_2$)$_3$CH$_3$ | 13.6 | 5.7 |
| R$^D$—⟨phenyl⟩—⟨phenyl⟩—O(CH$_2$)$_2$—OC(CH$_3$)$_3$ | 5.0 | 1.9 |

TABLE D.2

| Boronic acid reactant | mass (g) | [CH₃CO₂-C₆H₄-I] mass (g) | Product | mass (g) |
|---|---|---|---|---|
| (HO)₂B-C₆H₄-C₆H₄-O(CH₂)₃CH₃ | 5.0 | 3.2 | CH₃CO₂-C₆H₄-C₆H₄-C₆H₄-O(CH₂)₃CH₃ | 4.2 |
| (HO)₂B-C₆H₄-C₆H₄-O(CH₂)₄CH₃ | 6.0 | 3.7 | CH₃CO₂-C₆H₄-C₆H₄-C₆H₄-O(CH₂)₄CH₃ | 5.2 |
| (HO)₂B-C₆H₄-C₆H₄-O(CH₂)₅CH₃ | 3.4 | 2.8 | CH₃CO₂-C₆H₄-C₆H₄-C₆H₄-O(CH₂)₅CH₃ | 3.5 |
| (HO)₂B-C₆H₄-C₆H₄-O(CH₂)₂—O(CH₂)₃CH₃ | 3.7 | 3.6 | CH₃CO₂-C₆H₄-C₆H₄-C₆H₄-O(CH₂)₂—O(CH₂)₃CH₃ | 3.7 |
| (HO)₂B-C₆H₄-C₆H₄-O(CH₂)₂—OC(CH₃)₃ | 1.8 | 1.5 | CH₃CO₂-C₆H₄-C₆H₄-C₆H₄-O(CH₂)₂—OC(CH₃)₃ | 2.2 |

Preparation 5

The following activated esters were prepared substantially in accordance with Procedure G, detailed above.

TABLE G

| Carboxylic acid | mass (g) | mass (g) activated ester (2,4,5-trichlorophenyl ester) |
|---|---|---|
| 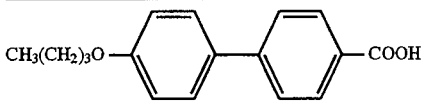 CH$_3$(CH$_2$)$_3$O—⬡—⬡—COOH | 1.9 | 1.8 |
| 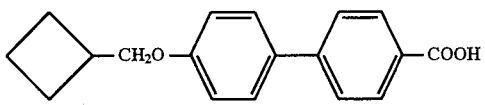 ▱—CH$_2$O—⬡—⬡—COOH | 4.2 | 4.4 |
| 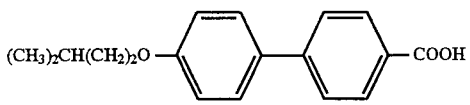 (CH$_3$)$_2$CH(CH$_2$)$_2$O—⬡—⬡—COOH | 3.0 | 1.7 |
| 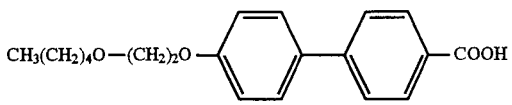 CH$_3$(CH$_2$)$_4$O—(CH$_2$)$_2$O—⬡—⬡—COOH | 2.2 | 1.3 |
| 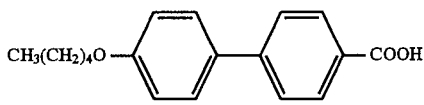 CH$_3$(CH$_2$)$_4$O—⬡—⬡—COOH | 5.7 | 5.1 |
| 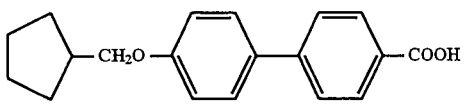 ⬠—CH$_2$O—⬡—⬡—COOH | 4.4 | 3.1 |
| 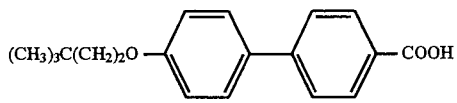 (CH$_3$)$_3$C(CH$_2$)$_2$O—⬡—⬡—COOH | 2.3 | 2.6 |
|  (CH$_3$CH$_2$)$_2$CHCH$_2$O—⬡—⬡—COOH | 1.5 | 0.8 |
| 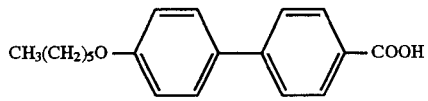 CH$_3$(CH$_2$)$_5$O—⬡—⬡—COOH | 5.3 | 4.8 |
|  ⬡—(CH$_2$)$_2$O—⬡—⬡—COOH | 3.1 | 1.0 |
| 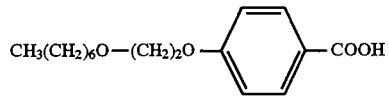 CH$_3$(CH$_2$)$_6$O—(CH$_2$)$_2$O—⬡—COOH | 5.6 | 2.9 |
| 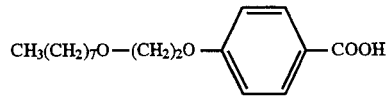 CH$_3$(CH$_2$)$_7$O—(CH$_2$)$_2$O—⬡—COOH | 7.8 | 6.6 |
| 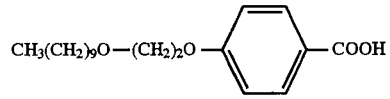 CH$_3$(CH$_2$)$_9$O—(CH$_2$)$_2$O—⬡—COOH | 6.4 | 1.3 |

TABLE G-continued

| Carboxylic acid | mass (g) | mass (g) activated ester (2,4,5-trichlorophenyl ester) |
|---|---|---|
| CH₃(CH₂)₃—⟨phenyl⟩—CH₂O—⟨phenyl⟩—COOH | 4.0 | 3.2 |
| CH₃(CH₂)₃O—⟨phenyl⟩—O—⟨phenyl⟩—COOH | 5.8 | 1.4 |
| CH₃(CH₂)₅O—⟨phenyl⟩—O—⟨phenyl⟩—COOH | 3.8 | 2.4 |
| CH₃(CH₂)₃O—⟨phenyl⟩—⟨phenyl⟩—C≡C—⟨phenyl⟩—COOH | 2.9 | 2.5 |
| CH₃(CH₂)₃O—(CH₂)₂O—⟨phenyl⟩—⟨phenyl⟩—C≡C—⟨phenyl⟩—COOH | 2.0 | 1.5 |
| (CH₃)₃CO—(CH₂)₂O—⟨phenyl⟩—⟨phenyl⟩—C≡C—⟨phenyl⟩—COOH | 2.0 | 1.3 |
| CH₃(CH₂)₃O—⟨phenyl⟩—C≡C—⟨phenyl⟩—⟨phenyl⟩—COOH | 6.5 | 5.2 |
| CH₃(CH₂)₃O—(CH₂)₂O—⟨phenyl⟩—C≡C—⟨phenyl⟩—⟨phenyl⟩—COOH | 4.9 | 5.2 |
| (CH₃)₃CO—(CH₂)₂O—⟨phenyl⟩—C≡C—⟨phenyl⟩—⟨phenyl⟩—COOH | 4.6 | 2.1 |
| CH₃(CH₂)₂—⟨piperidine⟩—N—(CH₂)₂O—⟨phenyl⟩—⟨phenyl⟩—COOH | 3.3 | 1.5 |
| ⟨phenyl⟩—CH₂—⟨piperidine⟩—N—(CH₂)₂O—⟨phenyl⟩—⟨phenyl⟩—COOH | 3.0 | 2.3 |
| CH₃(CH₂)₅—N⟨piperidine⟩—(CH₂)₂O—⟨phenyl⟩—⟨phenyl⟩—COOH | 1.0 | 1.0 |
| ⟨cyclohexyl⟩—CH₂—N⟨piperidine⟩—(CH₂)₂O—⟨phenyl⟩—⟨phenyl⟩—COOH | 2.0 | 0.8 |
| ⟨cyclohexyl⟩—⟨piperidine⟩—N—(CH₂)₂O—⟨phenyl⟩—⟨phenyl⟩—COOH | 7.2 | 0.8 |

TABLE G-continued

| Carboxylic acid | mass (g) | mass (g) activated ester (2,4,5-trichlorophenyl ester) |
|---|---|---|
| cyclohexyl-CH₂-piperidine-N-(CH₂)₂O-C₆H₄-C₆H₄-COOH | 7.5 | 7.3 |
| C₆H₅-C≡C-C₆H₄-C₆H₄-COOH | 2.0 | 0.6 |
| CH₃(CH₂)₃-C≡C-C₆H₄-C₆H₄-COOH | 1.1 | 0.6 |
| CH₃(CH₂)₅-C≡C-C₆H₄-COOH | 4.6 | 3.5 |
| CH₃(CH₂)₅-C=C-C₆H₄-COOH (trans) | 1.2 | 0.5 |
| CH₃(CH₂)₇-C≡C-C₆H₄-COOH | 11.1 | 13.2 |
| C₆H₅-C≡C-C₆H₄-COOH | 1.5 | 1.5 |
| CH₃(CH₂)₇-C≡C-(furan-O)-COOH | 8.3 | 13.2 |
| C₆H₅-C₆H₄-C₆H₄-COOH | 0.8 | 1.2 |
| CH₃(CH₂)₃O-C₆H₄-C₆H₄-C₆H₄-COOH | 3.3 | 4.8 |
| CH₃(CH₂)₄O-C₆H₄-C₆H₄-C₆H₄-COOH | 3.0 | 2.5 |
| CH₃(CH₂)₅O-C₆H₄-C₆H₄-C₆H₄-COOH | 2.3 | 3.9 |
| CH₃(CH₂)₃O-(CH₂)₂O-C₆H₄-C₆H₄-C₆H₄-COOH | 3.3 | 4.4 |
| (CH₃)₃CO-(CH₂)₂O-C₆H₄-C₆H₄-C₆H₄-COOH | 1.3 | 1.9 |

EXAMPLE 1

N-Acylation of Cyclic Peptide Nuclei

The N-acyl cyclic peptide derivatives listed in Table 3, below were prepared by dissolving Echinocandin B (A-30912A) nucleus (compound of formula IB where R', R", and R'" are each methyl, $R^{x1}$ and $R^{x2}$ are each hydroxy, $R^{y1}$, $R^{y2}$, $R^{y3}$, and $R_{y4}$ are each hydroxy, and R is hydroxy), and the activated ester (2,4,5-trichlorophenol ester) intermediates, described in Preparation 6, in 25–50 ml of dimethylformamide. The resultant reaction mixture was stirred for approximately 17–65 hours at room temperature and then the solvent was removed in vacuo to provide a residue. This residue was slurried in ether, collected by filtration, washed with methylene chloride and then dissolved in methanol or a 1:1 (v/v) acetonitrile/water mixture. The resultant solution is subjected to reverse phase HPLC (C18; eluent of 20–40% aqueous acetonitrile containing 0.5% monobasic ammonium phosphate (w/v); 20 ml/min.; 230 nm). After removing the unreacted A30912A nucleus, the desired product is eluted from the column using an eluent of aqueous acetonitrile. The fractions containing the desired product are combined and then concentrated in vacuo or lyophilized to provide the desired acylated nucleus. The product may be analyzed using reverse phase HPLC (C18; 40% aqueous acetonitrile containing 0.5% monobasic ammonium phosphate (w/v); 2 ml/min; 230 nm) or using MS (FAB).

For example, the compound depicted in Table 3II, below, was prepared substantially according to this procedure, using 348.1 g (60.2 mmol) of the A30912A nucleus, 26.0 g (48.2 mmol) of the 2,4,5-trichlorophenol ester of [[(4"-pentyloxy)-1,1':4',1"-terphenyl]-4-carboxylic acid in 8.5 liter of dimethylformamide. The resultant reaction mixture was allowed to react for approximately forty eight hours and then concentrated in vacuo and purified using HPLC to provide 18 g of compound 3II.

MS (FAB): 1140.5103 ($M^{+1}$).

Compounds A-PP (listed in Table 3 below) were prepared substantially as described above.

TABLE 3

| Ex. No. | R₂ | | Ester (mg) | A30912A Nucleus (g) | Product (mg) | MS (FAB) | HPLC R$_T$ (min) |
|---|---|---|---|---|---|---|---|
| 3A | CH$_3$(CH$_2$)O— | —phenyl-phenyl-C(O)— | 561 | 1.0 | 235 | 1072* | 4.08 |
| 3B | cyclobutyl-CH$_2$O— | —phenyl-phenyl-C(O)— | 576 | 1.0 | 294 | 1062* | 4.46 |
| 3C | (CH$_3$)$_2$CH(CH$_2$)$_2$O— | —phenyl-phenyl-C(O)— | 579 | 1.0 | 355 | 1086* | 5.75 |
| 3D | CH$_3$(CH$_2$)$_4$O—(CH$_2$)$_2$O— | —phenyl-phenyl-C(O)— | 634 | 1.0 | 359 | 1130* | 5.79 |
| 3E | CH$_3$(CH$_2$)$_4$O— | —phenyl-phenyl-C(O)— | 289 | 0.5 | 81 | 1083* | 6.08 |
| 3F | cyclopentyl-CH$_2$O— | —phenyl-phenyl-C(O)— | 594 | 1.0 | 295 | 1098* | 6.44 |
| 3G | (CH$_3$)$_3$C(CH$_2$)$_2$O— | —phenyl-phenyl-C(O)— | 596 | 1.0 | 270 | 1100* | 8.15 |
| 3H | (CH$_3$CH$_2$)$_2$CHCH$_2$O— | —phenyl-phenyl-C(O)— | 596 | 1.0 | 359 | 1100* | 9.13 |
| 3I | CH$_3$(CH$_2$)$_5$O— | —phenyl-phenyl-C(O)— | 596 | 1.0 | 301 | 1100* | 10.24 |

TABLE 3-continued
| Ex. No. | R₂ | Ester (mg) | A30912A Nucleus (g) | Product (mg) | MS (FAB) | HPLC R_T (min) |
|---|---|---|---|---|---|---|
| 3J | 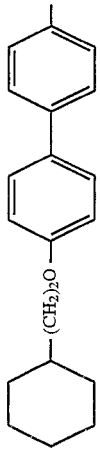 | 629 | 1.0 | 180 | 1104** | — |
| 3K | 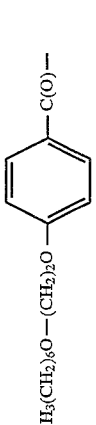 | 287 | 0.5 | 110 | 1082* | 4.52 |
| 3L | 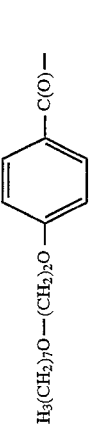 | 593 | 1.0 | 307 | 1096* | 7.28 |
| 3M | 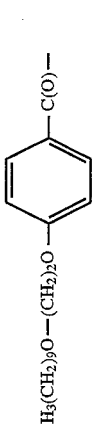 | 313 | 0.5 | 104 | 1124* | 19.04 |
| 3N | 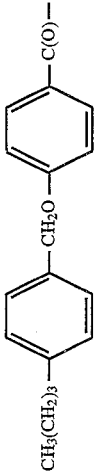 | 579 | 1.0 | 293 | 1032* | 6.14 |
| 3O | 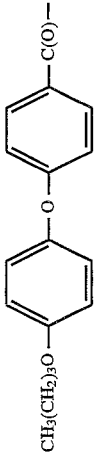 | 291 | 0.5 | 98 | 1088* | 3.96 |
| 3P | 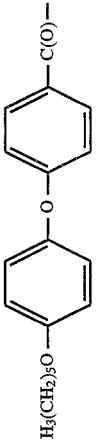 | 616 | 1.0 | 341 | 1116* | 11.56 |
| 3Q | 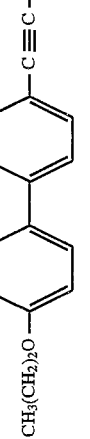 | 2400 | 3.2 | 3000 | 1194.5213† | — |
| 3R | 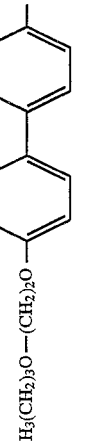 | 1300 | 1.5 | 2400 | 1194.5247† | — |

TABLE 3-continued

| Ex. No. | R₂ | Ester (mg) | A30912A Nucleus (g) | Product (mg) | MS (FAB) | HPLC R$_T$ (min) |
|---|---|---|---|---|---|---|
| 3S | (CH₃)₃CO—(CH₂)₂O— [structure with biphenyl-C≡C-C(O)—] | 4600 | 7.4 | 1300 | 1126.5025† | — |
| 3T | CH₃(CH₂)₂ [piperidine-N—(CH₂)₂O-biphenyl-C(O)—] | 683 | 1.0 | 384 | 1147** | 1.92 |
| 3U | [benzyl-piperidine-N—(CH₂)₂O-biphenyl-C(O)—] | 1490 | 2.0 | 116 | 1195** | 2.06 |
| 3V | CH₃(CH₂)₅—N [cyclohexyl-(CH₂)₂O-biphenyl-C(O)—] | 1000 | 1.2 | 194 | 1190*** | 2.41 |
| 3W | [cyclohexyl-CH₂—N—(CH₂)₂O-biphenyl-C(O)—] | 734 | 0.9 | 303 | 1202* | 2.21 |
| 3X | [cyclohexyl-cyclohexyl-(CH₂)₂O-biphenyl-C(O)—] | 810 | 1.0 | 230 | 1187** | 2.52 |
| 3Y | [cyclohexyl-CH₂—N—(CH₂)₂O-biphenyl-C(O)—] | 750 | 1.0 | 126 | 1201** | 3.50 |
| 3Z | [phenyl-C≡C-biphenyl-C(O)—] | 596 | 1.0 | 190 | 1078** | 6.30 |
| 3AA | CH₃(CH₂)₃—C≡C-biphenyl-C(O)— | 571 | 1.0 | 295 | 1058** | 7.91 |

TABLE 3-continued

| Ex. No. | R₂ | Ester (mg) | A30912A Nucleus (g) | Product (mg) | MS (FAB) | HPLC R_T (min) |
|---|---|---|---|---|---|---|
| 3BB | CH₃(CH₂)₅—C≡C—⟨C₆H₄⟩—C(O)— | 511 | 1.0 | 322 | 1032* | 5.10 |
| 3CC | CH₃(CH₂)₅—CH=CH—⟨C₆H₄⟩—C(O)— (trans) | 514 | 1.0 | 287 | 1034* | 6.14 |
| 3DD | CH₃(CH₂)₇—C≡C—⟨C₆H₄⟩—C(O)— | 546 | 1.0 | 285 | 1060* | 12.48 |
| 3EE | C₆H₅—C≡C—⟨C₆H₄⟩—C(O)— | 501 | 1.0 | 218 | 1002** | 2.53 |
| 3FF | CH₃(CH₂)₇—C≡C—⟨furan⟩—C(O)— | 534 | 1.0 | 215 | 1050*** | 7.59 |
| 3GG | ⟨biphenyl⟩—C(O)— | 566 | 1.0 | 81 | 1054** | 3.89 |
| 3HH | CH₃(CH₂)₄O—⟨biphenyl⟩—C(O)— | 4600 | 7.4 | 1300 | 1126.5025† | — |
| 3II | CH₃(CH₂)₄O—⟨biphenyl⟩—C(O)— | 2500 | 3.7 | 5100 | 1140.5103† | — |
| 3JJ | CH₃(CH₂)₅O—⟨biphenyl⟩—C(O)— | 3500 | 5.0 | 1400 | 1154.5343†† | — |

TABLE 3-continued

| Ex. No. | R₂ | Ester (mg) | A30912A Nucleus (g) | Product (mg) | MS (FAB) | HPLC R_T (min) |
|---|---|---|---|---|---|---|
| 3KK | CH₃(CH₂)₃O—(CH₂)₂O— [biphenyl-C(O)—] | 4400 | 6.7 | 6500 | 1170.5234† | — |
| 3LL | (CH₃)₃CO—(CH₂)₂O— [biphenyl-C(O)—] | 1900 | 2.9 | 1400 | 1170.5261† | — |
| 3MM | CH₃(CH₂)₂O— [phenyl-C≡C-phenyl-C(O)—] | 5200 | 6.9 | 1400 | 1142.4951† | — |
| 3NN | (CH₃)₃CO—(CH₂)₂O— [phenyl-C≡C-phenyl-C(O)—] | 2100 | 2.5 | 2000 | 1200.5336† | — |
| 3OO | CH₃(CH₂)₃O—(CH₂)₂O— [phenyl-C≡C-phenyl-C(O)—] | 5200 | 6.4 | 1100 | 1194.5282† | — |
| 3PP | [fluorenyl-C≡C-phenyl-phenyl-C(O)—] | 1800 | 2.6 | 200 | 1166.4758† | — |

*(m − 1) + [Na]†; (m + 1); *m + [Na]†; †m + 1; ††m + [Li]†.

EXAMPLE 2

Dideoxycilofungin

To a suspension of 10.00 g (9.71 mmol of cilofungin in 100 ml of methylene chloride, was added a solution of 96 ml (602 mmol) of triethylsilane in 50 ml of methylene chloride. Then, a solution of 46.4 ml (602 mmol) of trifluoroacetic acid in 50 ml of methylene chloride was slowly added, over 15 minutes. The resultant solution was stirred at room temperature for approximately two hours and then concentrated in vacuo to provide a residue. This residue was triturated with diethyl ether and then purified using reverse phase HPLC (C18; gradient eluent of 10–20% acetonitrile in water (v/v); 500 psi). The fractions containing the desired compound were combined, concentrated in vacuo, and then lyophilized from p-dioxane to provide the desired titled compound.

Yield: 6.66 g (68.7%).

MS (FAB) for $C_{49}H_{72}N_7O_{15}$ Calc. 998.5086; Found: 998.512.

UV: $\lambda(EtOH)nm(\epsilon)$ 202.60(61012), 256.20(18569).

EXAMPLE 3

Preparation of the dideoxy compound where R', R", and R'" are each methyl, $R^{x1}$ and $R^{x2}$ are each hydroxy, $R^{y1}$, $R^{y2}$, $R^{y3}$, $R^{y4}$ are each hydroxy, R is hydroxy and $R_2$ is the acyl group depicted in Table 3II poured into a large volume of water (approximately 1 liter) resulting in the precipitation of a white solid. This solid was isolated by filtration through a sintered glass funnel, washed with diethyl ether and then dried in vacuo at 55° C. to provide 3.718 g of the titled compound. The funnel was washed with methanol to collect the remaining solid, which was dried in vacuo to provide an additional 0.154 g of the titled compound.

Yield: 3.872 g (79%).

MS (FAB): m/e 1108.7 (M)

HPLC:(eluent of 55% acetonitrile; 2 ml/min.; 280 nm): $R_T$=6.43 min.

EXAMPLE 4

Preparation of dideoxy cyclic hexapeptides

The following dideoxy compounds were prepared substantially in accordance with the procedure detailed in Example 3 using the designated amounts of a compound of formula IC where R', R" and R'" are methyl, $R^{x1}$ and $R^{x2}$ are hydroxy, $R^{y1}$, $R^{y2}$, $R^{y3}$ and $R^{y4}$ are hydroxy, R is hydroxy and $R_2$ is as designated, triethylsilane (TES) and trifluoroacetic acid (TFA).

TABLE 4

| Ex. No. | $R_2$ | formula IC (g) | TES (g) | TFA (g) | Yield (g) |
|---|---|---|---|---|---|
| A | —C(=O)—(C₁₀H₂₀)—O—(biphenyl) | 0.500 | 0.256 | 0.251 | 0.095 |
| B | —C(=O)—CH(C₁₂H₂₅)—O—(biphenyl) | 0.500 | 2.47 | 2.42 | 0.063 |
| C | —C(=O)—(naphthyl)—O—C₁₀H₂₁ | 0.500 | 2.63 | 2.57 | 0.392 |
| D | —C(=O)—(biphenyl)—O—CH₂CH₂—N(piperidinyl)—CH₂—(cyclohexyl) | 2.00 | 9.49 | 9.72 | 1.47 |
| E | —C(=O)—(biphenyl)—O—C₆H₁₃ | 0.500 | 3.50 | 3.44 | 0.291 |

To a mixture of 5 g (4.4 mmol) of the compound of Table 3II and 17 ml of trifluoroacetic acid in 250 ml of methylene chloride, was added 35 ml of triethylsilane. When the reaction was substantially complete, as indicated by HPLC (C18, eluent of 55% acetonitrile; 2 ml/min; 280 nm; $R_T$ (starting material)=4.19 min.; $R_T$ (product)=6.40 min.), the reaction mixture was concentrated in vacuo to provide a solid. This solid was slurried in 100 ml of 50% aqueous acetone and then dissolved by adjusting the pH of the mixture to approximately pH 7. The resultant solution was

EXAMPLE 5

Preparation of the Compound where R', R", end R'" are each methyl, $R^{x1}$ and $R^{x2}$ are each hydroxy, $R^{y1}$, $R^{y2}$, $R^{y3}$, $R^{y4}$ are each hydroxy, $R_0$ is ethylphosphonate and $R_2$ is the acyl group depicted in Table 3II A. Protection To a solution of 2.00 g (1.75 mmol) of the compound of Table 3II in 50 ml of dioxane at room temperature, was added 25 ml (175 mmol) of 2-(trimethylsilyl)ethanol and p-toluenesulfonic acid (15 mol percent). The resultant reaction mixture was allowed to react at room temperature for approximately three hours. When the reaction was substantially complete, as indicated by HPLC, the reaction was quenched with solid sodium bicarbonate and filtered. The desired titled compound was isolated from the filtrate using reverse phase HPLC (50% acetonitrile/50% water; 50 ml/min.; 280 nm).

Yield: 807 mg.

B. Formation of ethyl phosphonate derivative

To a cold (0° C.) solution of 234.1 mg (0.191 mmol) of the titled compound of Example 5A in 10 ml of tetrahydrofuran, was added 0.21 ml (0.210 mmol) of a 1.0 M solution of lithium bis(trimethylsilyl)amide (LHNDS) in hexanes, dropwise. The resultant mixture was allowed to stir for approximately twenty minutes followed by the dropwise addition of 24.5 µl (0.223 mmol) of ethylphosphonic dichloride. The reaction mixture was stirred for approximately thirty minutes, quenched with 1 ml of water and then concentrated in vacuo to provide a white solid.

Yield: 42 mg. HPLC (50% acetonitrile/50% water; 50 ml/min.; 280 nm): $R_T$=1.37

C. Deprotection

To a mixture of 40.0 mg (0.028 mmol) of the titled compound of Example 5B in 20 ml of methylene chloride, was added 35 µl (0.28 mmol) of boron trifluoride etherate, dropwise. The resultant reaction mixture was allowed to react for approximately thirty minutes and then was quenched with 1.0 ml of water, resulting in the formation of a white precipitate. The reaction mixture was triturated with diethyl ether and then filtered to provide a light yellow solid.

Yield: 12 mg.

MS (FAB): 1238.6 (M+Li).

EXAMPLE 6

Preparation of the compound where R', R", and R'" are each methyl, $R^{x1}$ and $R^{x2}$ are each hydroxy, $R^{y1}$, $R^{y2}$, $R^{y3}$, $R_{y4}$ are each hydroxy, $R_0$ is methylphosphonate and $R_2$ is the acyl group depicted in Table 3II A. Formation of methyl phosphonate derivative The subtitled compound was prepared substantially in accordance with the procedure detailed in Example 5B, above using 271.1 mg (0.221 mmol) of the titled compound of Example 5A, 0.24 ml (0.24 mmol) of a 1.0M solution of LHMDS in hexanes and 35.3 mg (0.266 mmol of methylphosphonic dichloride in 10 ml of tetrahydrofuran to provide 40 mg of crude material that was used without further purification.

B. Deprotection

The subtitled compound was prepared substantially in accordance with the procedure detailed in Example 5C, using the compound isolated in Example 6A and 35 µl of (0.28 mmol) of boron trifluoride etherate to provide a white/gray solid.

MS (FAB): 1200.5 (M–$H_2O$).

EXAMPLE 7

Preparation of the compound where R', R", and R'" are each methyl, $R^{x1}$ and $R^{x2}$ are each hydroxy, $R^{y1}$, $R^{y2}$, $R^{y3}$, $R^{y4}$ are each hydroxy, $R_0$ is phenylphosphonate and $R_2$ is the acyl group depicted in Table 3II A. Formation off phenyl phosphonate derivative The subtitled compound was prepared substantially in accordance with the procedure detailed in Example 5B, above, using 359.6 mg (0.294 mmol) of the titled compound of Example 5A, 0.333 ml (0.323 mmol) of a 1.0M solution of LHMDS in hexanes and 50 µl of phenylphosphonic dichloride to provide 52 mg of crude material which was used without further purification.

B. Deprotection

The subtitled compound was prepared substantially in accordance with the procedure detailed in Example 5C, using the compound isolated in Example 6A and 361 µl of boron trifluoride etherate to provide a yellowish solid.

Yield: 32 mg.

MS (FAB): 1262.4 (M–$H_2O$).

EXAMPLE 8

Preparation of the compound where R', R", and R'" are each methyl, $R^{x1}$ and $R^{x2}$ ere each hydrogen, $R^{y1}$, $R^{y2}$, $R^{y3}$, $R^{y4}$ are each hydroxy, $R_0$ is isopropylphosphate and $R_2$ is the acyl group depicted in Table 3II A. Isopropyldichlorophosphate To a solution of 1.55 ml (16.6 mmol) of phosphorous oxychloride in 5 ml of carbon tetrachloride, was added 1.28 ml (16.6 mmol) of isopropanol, under nitrogen, resulting in an increase in temperature. An ice bath was used as necessary to keep the temperature between 20° C. and 35° C. The reaction mixture was allowed to react for approximately seven hours at room temperature, under nitrogen. The resultant mixture was concentrated in vacuo to provide a clear oil.

Yield: 1.9 g (65%).

B. Formation of isopropyl phosphate derivative

To a cold (0° C.) solution containing 0.5 g (0.45 mmol) of the titled compound of Example 3 in 10 ml of tetrahydrofuran and 54 µl (0.54 mmol) of lithium trimethylsilanolate (LiOTMS), was added 88 mg (0.5 mmol) of the subtitled compound of Example 8A. The resultant reaction mixture was stirred for approximately ten minutes. Additional LiOTMS was added to the reaction mixture until the pH of the mixture was basic. When the reaction was substantially complete, as indicated by HPLC, the reaction was quenched with water, stirred for approximately one hour and then concentrated in vacuo to provide a yellow solid. This solid was purified using HPLC (eluent of 45% acetonitrile/45% water/10% trifluoroacetic acid (1% aqueous solution)) to provide a white solid.

Yield: 105 mg.

MS (FAB): 1230.4 (M⁺)

EXAMPLE 9

Preparation of the compound where R', R", and R'" are each methyl, $R^{x1}$ and $R^{x2}$ are each hydrogen, $R^{y1}$, $R^{y2}$, $R^{y3}$, $R^{y4}$ are each hydroxy, $R_0$ is butylphosphate and $R_2$ is the acyl group depicted in Table 3II A. Butyldichlorophosphate The desired subtitled compound was prepared substantially in accordance with the procedure detailed in Example 8A, using 1.25 ml (13.5 mmol) of phosphorous oxychloride, 1 g (13.5 mmol) of butanol in 5 ml of carbon tetrachloride to provide a colorless oil.

Yield: 2.3 g (89%).

B. Formation of butyl phosphate derivative

The desired subtitled compound was prepared substantially in accordance with the procedure detailed in Example 85, using 0.5 g (0.45 mmol) of the titled compound of Example 3, LiOTMS and 95 mg (0.50 mmol) of the subtitled compound of Example 9A to provide a yellow solid. This solid was purified using reverse phase HPLC (gradient eluent of 45% acetonitrile/45% water/10% (1% aqueous) trifluoroacetic acid→→50% acetonitrile/40% water/10% (1% aqueous) trifluoroacetic acid) to provide a 126 mg of the desired compound.

MS (FAB): 1244.4 (M⁺)

EXAMPLE 10

Preparation of the compound where R', R" and R'" are each methyl, $R^{x1}$ and $R^{x2}$ are each hydrogen, $R^{y1}$, $R^{y2}$, $R^{y3}$, $R^{y4}$ are each hydroxy, $R_0$ is methylphosphate and $R_2$ is the acyl group depicted in Table 3II To a mixture of 500 mg (0.45 mmol) of the titled compound of Example 3 and 0.5 mL (0.5 mmol) of LiOTMS in 5 ml of tetrahydrofuran, was added 0.075 ml (0.75 mmol) of methyl dichlorophosphate resulting in the dissolution of solid material. The reaction was monitored by HPLC (eluent of 70% acetonitrile; 2 ml/min.; 280 nm) resulting in the addition of an additional 0.7 ml of LiOTMS and 0.02 ml of methyl dichlorophosphate to the reaction mixture. When the reaction was substantially complete, as indicated by HPLC (eluent of 50% acetonitrile containing 0.1% trifluoroacetic acid; 2 ml/min.; 280 nm), the desired compound was isolated using HPLC (eluent of 40% acetonitrile containing 0.1% trifluoroacetic acid; 90 ml/min.; 280 nm). The fractions containing the desired compound were combined and concentrated in vacuo to provide 232 mg of the titled compound (81% pure by HPLC). This compound was purified using HPLC (step gradient eluent of 30%→35%→40% acetonitrile containing 0.1% trifluoroacetic acid; 90 ml/min.; 280 nm) to provide 109 mg of the titled compound (94% pure).

MS (FAB): m/e 1202.6 (M⁺).

EXAMPLE 11

Preparation of the compound where R', R", and R'" are each methyl, $R^{x1}$ and $R^{x2}$ are each hydrogen, $R^{y1}$, $R^{y2}$, $R^{y3}$, $R^{y4}$ are each hydroxy, $R_0$ is hexylphosphonate and $R_2$ is the acyl group depicted in Table 3II To a cold (0° C.) mixture of 1 g (0.902 mmol) of the titled compound of Example 3 in 5 ml of tetrahydrofuran, was added 1.35 ml of a 1M solution of LHMDS in tetrahydrofuran (1.35 mmol), dropwise. After stirring the resulting mixture for approximately thirty minutes, 309 µl (1.804 mmol) of hexyldichlorophosphate was added and the reaction mixture was allowed to warm to room temperature, followed by the addition of water. The resultant reaction mixture was reduced to dryness in vacuo to provide the desired titled compound.

Yield: 102 mg.
MS (FAB): Calcd: 1262.5978 (M⁺Li);
Found: 1262.5979 (M⁺ᴸⁱ).

EXAMPLE 12

Preparation of the compound where R', R", and R'" are each methyl, $R^{x1}$ and $R^{x2}$ are each hydrogen, $R^{y1}$, $R^{y2}$, $R^{y3}$, $R^{y4}$ are each hydroxy, $R_0$ is methylphosphonate and $R_2$ is the acyl group depicted in Table 3II The titled compound was prepared substantially in accordance with the procedure detailed in Example 11, using 221.9 mg (0.200 mmol) of the titled compound of Example 3 and 0.240 ml of a 1M solution of LHMDS in hexanes (0.240 mmol) and 35 mg (0.26 mmol) of methyl phosphonic dichloride in 20 ml of tetrahydrofuran.

Yield: 44 mg.
MS (FAB): 1192.2 (M+Li)

EXAMPLE 13

Preparation of the compound where R', R", and R'" are each methyl, $R^{x1}$ and $R^{x2}$ are each hydroxy, $R^{y1}$, $R^{y2}$, $R^{y3}$, $R^{y4}$ are each hydroxy, $R_0$ is methylphosphate and $R_2$ is the acyl group depicted in Table 3II A. Formation of methyl phosphate derivative To a cold (0° C.) mixture of 400 mg (0.32 mmol) of the subtitled compound of Example 5A and 0.36 mL (0.36 mmol) of LiOTMS (1M solution in methylene chloride) in 5 ml of tetrahydrofuran, under nitrogen, was added 0.04 ml (0.4 mmol) of methyl dichlorophosphate. When the reaction was substantially complete, as indicated by HPLC (eluent of 80% acetonitrile; 2 ml/min.; 280 nm), several aliquots of lithium hydroxide were added to the mixture. The desired compound was isolated using HPLC (eluent of 60% acetonitrile containing 0.1% trifluoroacetic acid; 90 ml/min.; 280 nm). The fractions containing the desired compound were combined and concentrated in vacuo to provide 129.8 mg of the subtitled compound.

Yield: 30%.
HPLC (eluent of 65% acetonitrile containing 0.1% trifluoroacetic acid; 2 ml/min.; 280 nm): $R_T$=4.28 min.

B. Deprotection

To a cold (0° C.) mixture of 118 mg (0.09 mmol) of the subtitled compound of Example 13A in 3 ml of methylene chloride, was added 35 µl (0.28 mmol) of boron trifluoride etherate. The resultant reaction mixture was allowed to react for approximately ten minutes and then was quenched with several drops of water, resulting in the formation of a white precipitate. The reaction mixture was concentrated in vacuo to provide a residue. This residue was slurried in diethyl ether and then filtered to provide a solid which was dried in vacuo. The resultant product was determined to be 92% pure using HPLC (eluent of 50% acetonitrile containing 1% trifluoroacetic acid; 2 ml/min.; 280 nm; $R_T$=3.92 min)

Yield: 88 mg (80%).
MS (FAB): 1216.4 (M–H₂O) 1256.3 (M+Na).

EXAMPLE 14

Preparation of the compound where R', R", and R'" are each methyl, $R^{x1}$ and $R^{x2}$ are each hydroxy, $R^{y1}$, $R^{y2}$, $R^{y3}$, $R^{y4}$ are each hydroxy, $R_0$ is ethylphosphate and $R_2$ is the acyl group depicted in Table 3II A. Formation of ethyl phosphate derivative To a cold (0° C.) mixture of 400 mg (0.32 mmol) of the subtitled compound of Example 5A and 0.36 mL (0.36 mmol) of LiOTMS (1M solution in methylene chloride) in 5 ml of tetrahydrofuran, under nitrogen, was added 0.47 ml (0.4 mmol) of ethyl dichlorophosphate. When the reaction was substantially complete, as indicated by HPLC (eluent of 80% acetonitrile; 2 ml/min.; 280 nm), approximately 0.5 ml of water was added to the mixture, dropwise. The desired compound was isolated using HPLC (eluent of 60% acetonitrile containing 0.1% trifluoroacetic acid; 90 ml/min.; 280 nm). The fractions containing the desired compound were combined and concentrated in vacuo to provide a residue. This residue was slurried in diethyl ether and then filtered to provide 67.8 mg of a solid. This resultant product was determined to be 71% pure using HPLC (eluent of 65% acetonitrile containing 0.1% trifluoroacetic acid; 2 ml/min.; 280 nm; $R_T$=5.99 min.).

B. Deprotection

The desired titled compound was prepared substantially in accordance with the procedure detailed in Example 13B, using 67.8 mg of the subtitled compound of Example 14A and 0.1 ml (0.81 mmol) of the boron trifluoride etherate in methylene chloride. The resultant product was determined to be 89% pure using HPLC (eluent of 50% acetonitrile containing 0.1% trifluoroacetic acid; 2 ml/min.; 280 nm; $R_T$=5.85 min.)

Yield: 51 mg.
MS (FAB): 1230.3 (M–H$_2$O).

The compounds of formula I have improved properties over the previously known N-acyl cyclic peptide antifungal compounds. For example, the present compounds have increased oral bioavailability, an important property for a systemic antifungal compound. In addition, the present compounds have enhanced antifungal activity and enhanced water solubility, relative to previously known compounds.

The compounds of formula I exhibit antifungal and antiparasitic activity. For example, the compounds of formula I inhibit the growth of various infectious fungi including Candida spp. such as *C. albicans*, *C. parapsilosis*, *C. krusei*, *C. glabrata*, or *C. tropicalis*, *C. lusitaniae*; Torulopus spp. such as *T. glabrata*; Aspergillus spp. such as *A. fumigatus*; Histoplasma spp. such as *H. capsulatum*; Cryptococcus spp. such as *C. neoformans*; Blastomyces spp. such as *B. dermatitidis*; Fusarium spp., Trichophyton spp., *Pseudallescheria boydii*, *Coccidioides immits*, *Sporothrix schenckii* and the like.

Antifungal activity of a test compound is determined in vitro by obtaining the minimum inhibitory concentration (MIC) of the compound using a standard agar dilution test or a disc-diffusion test. The compound is then tested in vivo (in mice) to determine the effective dose of the test compound for controlling a systemic fungal infection.

Accordingly, the following compounds were tested for antifungal activity against *C. albicans*.

TABLE 5

| Minimal inhibitory concentration against C. albicans | |
|---|---|
| Example No. | MIC (µg/ml) |
| 5C | 0.312 |
| 6B | 1.25 |
| 7B | 2.5 |
| 8B | >80 |
| 9B | >80 |
| 10 | 0.312 |
| 11 | 1.25 |
| 12 | 0.039 |
| 13B | 0.625 |
| 14B | 0.625 |

In addition, the effective dose of the following compounds for controlling a systemic fungal infection (C. albicans) was tested in vivo (mice).

TABLE 5

| ED$_{50}$ (mouse) | |
|---|---|
| Example No. | ED$_{50}$ (mg/kg) |
| 5C | 1.25 |
| 6B | 1.58 |
| 7B | >2.5 |
| 8B | 1.02 |
| 9B | 0.39 |
| 10 | 0.47 |
| 11 | 0.312 |
| 12 | 0.79 |
| 13B | 1.86 |
| 14B | 1.38 |

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia (PCP) in AIDS and other immunocompromised patients. Other protozoans that are inhibited by compounds of formula I include Plasmodium spp., Leishmania spp., Trypanosoma spp., Cryptosporidium spp., Isospora spp., Cyclospora spp., Trichomnas spp., Microsporidiosis spp. and the like.

The compounds of formula I are active in vitro and in vivo and are useful in combating either systemic fungal infections or fungal skin infections. Accordingly, the present invention provides a method of inhibiting fungal activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parenterally, for example using intramuscular, subcutaneous, or intra-peritoneal injection, nasal, or oral means. In addition to these methods of administration, a compound of formula I may be applied topically for skin infections.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The present invention further provides a method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment. The compounds of formula I can be used prophylactically to prevent the onset of the infection which is caused by the organism *Pneumocystis carinii*, or alternatively they can be used to treat a host that has been infected with *Pneumocystis carinii*. A compound of formula I may be administered parenterally, for example using intramuscular, intravenous or intraperitoneal injection, orally or by inhaling directly into the airways of the lungs. A preferred mode of administration is inhalation of an aerosol spray formulation of a compound of formula I.

With respect to antiparasitic activity, the term "effective amount," means an amount of a compound of the present invention which is capable of inhibiting parasitic activity. An effective amount of the compound of formula I is from about 3 mg/kg of patient body weight to about 100 mg/kg. The amount administered may be in a single daily dose or multiple doses of, for example, two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that Pneumocystis pneumonia infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to Pneumocystis pneumonia can be treated with lower and less frequent prophylactic doses.

We claim:

1. A compound of formula I:

wherein:

R' is hydrogen, methyl or $NH_2C(O)CH_2-$;

R" and R''' are independently methyl or hydrogen;

$R^{x1}$, $R^{x2}$, $R^{y1}$, $R^{y2}$, $R^{y3}$, and $R^{y4}$ are independently hydroxy or hydrogen;

$R_0$ is a group of the formula $$-O-\overset{O}{\underset{OH}{P}}-R_1$$

$R_1$ is $C_1-C_6$ alkyl, $C_1-C_6$ alkoxy, phenyl, p-halo-phenyl, p-nitrophenyl, phenoxy, benzyl, p-halo-benzyl, or p-nitro-benzyl;

I) $R_2$ is a group of the formula where:

A) $R_3$ is $C_1-C_{12}$ alkyl, $C_1-C_6$ alkoxy or quinolyl;

B) $R_3$ is $-O-(CH_2)_m-[O-(CH_2)_n]_p-O-(C_1-C_{12}$ alkyl);

m and n are independently 2, 3 or 4;

p is 0 or 1; or

C) $R_3$ is —Y—($C_1$-$C_{12}$ alkyl);
 Y is —C≡C— or —CH=CH—; or

D) $R_3$ is —O—$(CH_2)_q$—G;
 q is 2, 3 or 4;
 G is $C_7$-$C_{10}$ bicycloalkyl or $C_7$-$C_{14}$ tricycloalkyl; or II) $R_2$ is a group of the formula

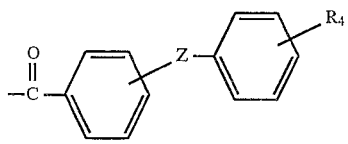

where:

Z is —O—, —C≡C—, —CH=CH—, —$CH_2$—$CH_2$—, —$CH_2$—, or a bond;

A) $R_4$ is hydrogen, $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, $C_2$-$C_{12}$ substituted alkynyl, $C_1$-$C_{12}$ alkoxy, $C_3$-$C_{12}$ cycloalkyl, $C_7$-$C_{10}$ bicycloalkyl, $C_7$-$C_{14}$ tricycloalkyl, $C_3$-$C_{12}$ cycloalkoxy, naphthyl, pyridyl, thienyl, benzothienyl, quinolyl or phenyl; or B) $R_4$ is phenyl substituted by amino, $C_1$-$C_{12}$ alkylthio, halo, $C_1$-$C_{12}$ alkyl, $C_2$-$C_{12}$ alkenyl, $C_2$-$C_{12}$ alkynyl, $C_1$-$C_{12}$ substituted alkyl, $C_2$-$C_{12}$ substituted alkenyl, $C_2$-$C_{12}$ substituted alkynyl, $C_1$-$C_{12}$ alkoxy, trifluoromethyl, phenyl, substituted phenyl, or phenyl substituted with a group of the formula —O—$(CH_2)_m$—[O—$(CH_2)_n]_p$—O—($C_1$-$C_{12}$ alkyl) where m, n and p are as defined above; or C) $R_4$ is $C_1$-$C_{12}$ alkoxy substituted with halo, $C_3$-$C_{12}$ cycloalkyl, $C_7$-$C_{10}$ bicycloalkyl, $C_7$-$C_{14}$ tricycloalkyl, $C_1$-$C_6$ alkoxy, $C_2$-$C_{12}$ alkynyl, amino, $C_1$-$C_4$ alkylamino, di($C_1$-$C_4$ alkyl) amino, formamido, $C_2$-$C_{12}$ alkanoylamino, or phenyl substituted with a group of the formula —O—$(CH_2)_m$—[O—$(CH_2)_n]_p$—O—($C_1$-$C_{12}$ alkyl) where m, n and p are as defined above; or D) $R_4$ is —O—$(CH_2)_r$—W—$R_5$;
 r is 2, 3 or 4;
 W is pyrrolidino, piperidino or piperazino;
 $R_5$ is hydrogen, $C_1$-$C_{12}$ alkyl, $C_3$-$C_{12}$ cycloalkyl, benzyl or $C_3$-$C_{12}$ cycloalkylmethyl; or E) $R_4$ is —$Y^1$—$R_6$;
 $Y^1$ is —C≡C— or —CH=CH—;
 $R_6$ is $C_3$-$C_{12}$ cycloalkyl, $C_7$-$C_{10}$ bicycloalkyl, $C_7$-$C_{14}$ tricycloalkyl, $C_3$-$C_{12}$ cycloalkenyl, naphthyl, benzothiazolyl, thienyl, indanyl, fluorenyl, or phenyl substituted with $C_1$-$C_{12}$ alkylthio, $C_2$-$C_{12}$ alkenyl, $C_2$-$C_{12}$ alkynyl, halo($C_1$-$C_6$ alkoxy) or a group of the formula —O—$(CH_2)_r$—W—$R_5$ where r, W and $R_5$ are as defined above; or $R_6$ is phenyl substituted with a group of the formula —O—$(CH_2)_m$—[O—$(CH_2)_n]_p$—O—($C_1$-$C_{12}$ alkyl) where m, n and p are as defined above; or F) $R_4$ is $C_1$-$C_{12}$ alkoxy substituted with a group of the formula —NHC(O)$R_7$;
 $R_7$ is $C_1$-$C_6$ alkoxy, or phenyl ($C_1$-$C_6$ alkoxy); or III) $R_2$ is a group of the formula

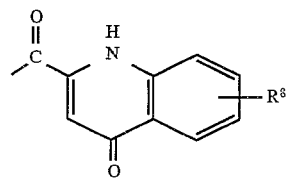

where $R^8$ is $C_1$-$C_{12}$ alkoxy or a group of the formula —O—$(CH_2)_m$—[O—$(CH_2)_n]_p$—O—($C_1$-$C_{12}$ alkyl) where m, n and p are as defined above; or IV) $R_2$ is a group of the formula

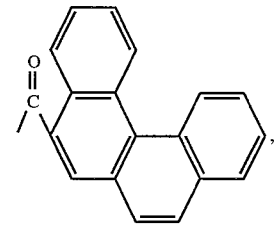

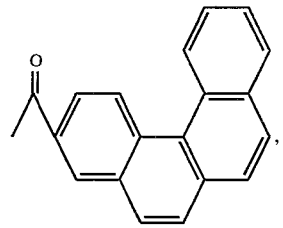

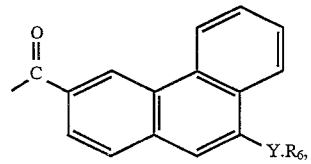

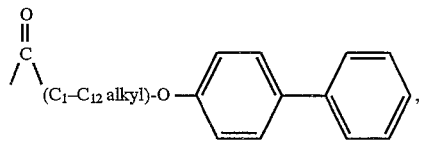

or

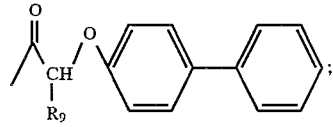

where:

Y and $R_6$ are as defined above;

$R_9$ is phenyl, $C_1$-$C_{12}$ alkyl, or $C_1$-$C_{12}$ alkoxy; or

V) $R_2$ is naphthoyl substituted with $R_4$ where $R_4$ is as defined above;

or a pharmaceutically acceptable salt thereof.

2. A compound according to claim 1 where:
 R', R", and R'" are each methyl;
 $R^{y1}$, $R^{y2}$, $R^{y3}$, $RY^4$ are each hydroxy;
or a pharmaceutically acceptable salt thereof.

3. A compound according to claim 2 where:
 $R^{x1}$ and $R^{x2}$ are hydrogen;
or a pharmaceutically acceptable salt thereof.

4. A compound according to claim 3 where:
R$_2$ is a group of the formula

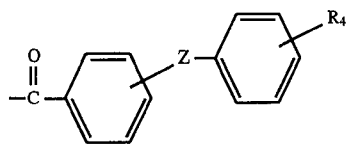

wherein:
Z is —C≡C—, —CH=CH—, —CH$_2$—CH$_2$—, or a bond;
A) R$_4$ is hydrogen, C$_1$-C$_{12}$ alkyl, C$_1$-C$_{12}$ substituted alkyl, C$_2$-C$_{12}$ alkenyl, C$_2$-C$_{12}$ substituted alkenyl, C$_2$-C$_{12}$ alkynyl, C$_2$-C$_{12}$ substituted alkynyl, C$_1$-C$_{12}$ alkoxy, C$_3$-C$_{12}$ cycloalkyl, C$_7$-C$_{10}$ bicycloalkyl, C$_7$-C$_{14}$ tricycloalkyl, C$_3$-C$_{12}$ cycloalkoxy, naphthyl, pyridyl, thienyl, benzothienyl, quinolyl or phenyl; or
B) R$_4$ is phenyl substituted by amino, C$_1$-C$_{12}$ alkylthio, halo, C$_1$-C$_{12}$ alkyl, C$_2$-C$_{12}$ alkenyl, C$_2$-C12 alkynyl, C$_1$-C$_{12}$ substituted alkyl, C$_2$-C$_{12}$ substituted alkenyl, C$_2$-C$_{12}$ substituted alkynyl, C$_1$-C$_{12}$ alkoxy, trifluoromethyl, phenyl, substituted phenyl, or a group of the formula —O—(CH$_2$)$_m$—[O—(CH$_2$)$_n$]$_p$—O—(C$_1$-C$_{12}$ alkyl) where m, n and p are as defined above; or
C) R$_4$ is C$_1$-C$_{12}$ alkoxy substituted with halo, C$_3$-C$_{12}$ cycloalkyl, C$_7$-C$_{10}$ bicycloalkyl, C$_7$-C$_{14}$ tricycloalkyl, C$_1$-C$_6$ alkoxy, C$_2$-C$_{12}$ alkynyl, amino, C$_1$-C$_4$ alkylamino, di(C$_1$-C$_4$ alkyl)amino, formamido, C$_2$-C$_{12}$ alkanoylamino, or phenyl substituted with a group of the formula —O—(CH$_2$)$_m$—[O—(CH$_2$)$_n$]$_p$—O—(C$_1$-C$_{12}$ alkyl) where m, n and p are as defined above; or
D) R$_4$ is —O—(CH$_2$)$_r$—W—R$_5$;
r is 2, 3 or 4;
W is pyrrolidino, piperidino or piperazino;
R$_5$ is hydrogen, C$_1$-C$_{12}$ alkyl, C$_3$-C$_{12}$ cycloalkyl, benzyl or C$_3$-C$_{12}$ cycloalkylmethyl; or
E) R$_4$ is —Y$^1$—R$_6$;
y$^1$ is —C≡C— or —CH=CH—;
R$_6$ is C$_3$-C$_{12}$ cycloalkyl, C$_7$-C$_{10}$ bicycloalkyl, C$_7$-C$_{14}$ tricycloalkyl, C$_3$-C$_{12}$ cycloalkenyl, naphthyl, benzothiazolyl, thienyl, indanyl, fluorenyl, or phenyl substituted with C$_1$-C$_{12}$ alkylthio, C$_2$-C$_{12}$ alkenyl, C$_2$-C$_{12}$ alkynyl, halo(C$_1$-C$_6$ alkoxy) or a group of the formula —O—(CH$_2$)$_r$—W—R$_5$ where r, W and R$_5$ are as defined above; or
R$_6$ is phenyl substituted with a group of the formula —O—(CH$_2$)$_m$—[—O—(CH$_2$)$_n$]$_p$—O—(C$_1$-C$_{12}$ alkyl) where m, n and p are as defined above; or
F) R$_4$ is C$_1$-C$_{12}$ alkoxy substituted with a group of the formula —NHC(O)R$_7$;
R$_7$ is C$_1$-C$_6$ alkoxy, or phenyl(C$_1$-C$_6$ alkoxy); or a pharmaceutically acceptable salt thereof.

5. A compound according to claim 4 where:
R$_2$ is a group of the formula

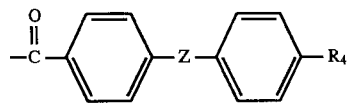

Z is —C≡C— or a bond;
or a pharmaceutically acceptable salt thereof.

6. A compound according to claim 5 where:
A) R$_4$ is hydrogen, C$_2$-C$_{12}$ alkynyl, C$_2$-C$_{12}$ substituted alkynyl, C$_1$-C$_{12}$ alkoxy, C$_3$-C$_{12}$ cycloalkoxy, or phenyl; or
B) R$_4$ is phenyl substituted by C$_1$-C$_{12}$ alkoxy, or a group of the formula —O—(CH$_2$)$_2$—O—(C$_1$-C$_6$ alkyl); or
C) R$_4$ is C$_1$-C$_{12}$ alkoxy substituted with C$_3$-C$_{12}$ cycloalkyl, C$_7$-C$_{14}$ tricycloalkyl, C$_1$-C$_6$ alkoxy, amino, di(C$_1$-C$_4$ alkyl)amino, formamido, or phenyl substituted with a group of the formula —O—(CH$_2$)$_2$—O—(C$_1$-C$_6$ alkyl); or
D) R$_4$ is —O—(CH$_2$)$_r$—W—R$_5$;
r is 2 or 3;
W is piperidino;
R$_5$ is hydrogen, C$_1$-C$_{12}$ alkyl, C$_3$-C$_{12}$ cycloalkyl, benzyl or C$_3$-C$_{12}$ cycloalkylmethyl; or
E) R$_4$ is —Y$^1$—R$_6$;
Y$^1$ is —C≡C—;
R$_6$ is phenyl substituted with C$_1$-C$_{12}$ alkylthio, C$_2$-C$_{12}$ alkenyl, C$_2$-C$_{12}$ alkynyl, halo(C$_1$-C$_6$ alkoxy);
or R$_6$ is phenyl substituted with a group of the formula —O—(CH$_2$)$_r$—W—R$_5$ where r, W and R$_5$ are as defined above;
or R$_6$ is phenyl substituted with a group of the formula —O—(CH$_2$)$_2$—O—(C$_1$-C$_6$ alkyl);
F) R$_4$ is C$_1$-C$_{12}$ alkoxy substituted with a group of the formula —NHC(O)R$_7$;
R$_7$ is C$_1$-C$_6$ alkoxy, or phenyl(C$_1$-C$_6$ alkoxy); or a pharmaceutically acceptable salt thereof.

7. A compound according to claim 6 where:
A) R$_4$ is C$_2$-C$_{12}$ alkynyl, C$_2$-C$_{12}$ substituted alkynyl, C$_1$-C$_{12}$ alkoxy, C$_3$-C$_{12}$ cycloalkoxy, or phenyl; or
B) R$_4$ is phenyl substituted by C$_1$-C$_{12}$ alkoxy, or a group of the formula —O—(CH$_2$)$_2$—O—(C$_1$-C$_6$ alkyl); or
C) R$_4$ is C$_1$-C$_{12}$ alkoxy substituted with C$_3$-C$_{12}$ cycloalkyl; or
D) R$_4$ is —O—(CH$_2$)$_r$—W—R$_5$;
r is 2 or 3;
W is piperidino;
R$_5$ is hydrogen, C$_1$-C$_{12}$ alkyl, C$_3$-C$_{12}$ cycloalkyl, benzyl or C$_3$-C$_{12}$ cycloalkylmethyl; or
E) R$_4$ is —Y$^1$—R$_6$;
Y$^1$ is —C≡C—;
R$_6$ is phenyl substituted with C$_1$-C$_{12}$ alkylthio, C$_2$-C$_{12}$ alkenyl, C$_2$-C$_{12}$ alkynyl, halo(C$_1$-C$_6$ alkoxy);
or R$_6$ is phenyl substituted with a group of the formula —O—(CH$_2$)$_r$—W—R$_5$ where r, W and R$_5$ are as defined above;
or R$_6$ is phenyl substituted with a group of the formula —O—(CH$_2$)$_2$—O—(C$_1$-C$_6$ alkyl);
or a pharmaceutically acceptable salt thereof.

8. A compound according to claim 7 where:
R$_4$ is C$_2$-C$_{12}$ alkynyl, C$_2$-C$_{12}$ substituted alkynyl, C$_1$-C$_{12}$ alkoxy, or phenyl; or
R$_4$ is phenyl substituted by C$_1$-C$_{12}$ alkoxy, or a group of the formula —O—(CH$_2$)$_2$—O—(C$_1$-C$_6$ alkyl); or
R$_4$ is —Y$^1$—R$_6$;
Y$^1$ is —C≡C—;
R$_6$ is phenyl substituted with a group of the formula —O—(CH$_2$)$_2$—O—(C$_1$-C$_6$ alkyl);
or a pharmaceutically acceptable salt thereof.

9. A compound according to claim 6 where R$_1$ is C$_1$-C$_4$ alkyl, C$_1$-C$_4$ alkoxy, phenyl, p-chloro-phenyl, p-bromo-phenyl, or p-nitro-phenyl, benzyl, p-chloro-benzyl, p-bromo-benzyl, or p-nitro-benzyl; or a pharmaceutically acceptable salt thereof.

10. A compound according to claim 9 where $R_1$ is methyl, ethyl, methoxy, ethoxy, phenyl, benzyl; or a pharmaceutically acceptable salt thereof.

11. A compound according to claim 8 where $R_1$ is $C_1$–$C_4$ alkyl, $C_1$–$C_4$ alkoxy, phenyl, p-chloro-phenyl, p-bromo-phenyl, or p-nitro-phenyl, benzyl, p-chloro-benzyl, p-bromo-benzyl, or p-nitro-benzyl; or a pharmaceutically acceptable salt thereof.

12. A compound according to claim 11 where $R_1$ is methyl, ethyl, methoxy, ethoxy, phenyl, benzyl; or a pharmaceutically acceptable salt thereof.

13. A compound according to claim 12 where $R_1$ is methyl or methoxy; or a pharmaceutically acceptable salt thereof.

14. The compound according to claim 13 where Z is a bond; $R_4$ is phenyl substituted by n-pentoxy; and $R_1$ is methyl; or a pharmaceutically acceptable salt thereof.

15. A pharmaceutical formulation comprising one or more pharmaceutically acceptable carriers, diluents or excipients and a compound of claim 1.

16. A pharmaceutical formulation according to claim 15 where the compound is one wherein:
R', R", and R'" are each methyl;
$R^{y1}$, $R^{y2}$, $R^{y3}$, $R^{y\,4}$ are each hydroxy;
or a pharmaceutically acceptable salt thereof.

17. A pharmaceutical formulation according to claim 16 where the compound is one wherein:
$R^{x1}$ and $R^{x2}$ are hydrogen;
or a pharmaceutically acceptable salt thereof.

18. A pharmaceutical formulation according to claim 17 where the compound is one wherein:
$R_2$ is a group of the formula

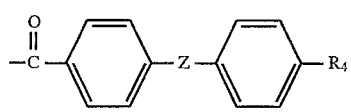

Z is —C≡C— or a bond;
or a pharmaceutically acceptable salt thereof.

19. A pharmaceutical formulation according to claim 18 where the compound is one wherein:
$R_4$ is $C_2$–$C_{12}$ alkynyl, $C_2$–$C_{12}$ substituted alkynyl, $C_1$–$C_{12}$ alkoxy, or phenyl; or
$R_4$ is phenyl substituted by $C_1$–$C_{12}$ alkoxy, or a group of the formula —O—$(CH_2)_2$—O—$(C_1$–$C_6$ alkyl); or
$R_4$ is y1 $R_6$;
$Y^1$ is —C≡C—;
$R_6$ is phenyl substituted with a group of the formula —O—$(CH_2)_2$—O—$(C_1$–$C_6$ alkyl);
or a pharmaceutically acceptable salt thereof.

20. A pharmaceutical formulation according to claim 19 where the compound is one wherein:
$R_1$ is $C_1$–$C_4$ alkyl, $C_1$–$C_4$ alkoxy, phenyl, p-chloro-phenyl, p-bromo-phenyl, or p-nitro-phenyl, benzyl, p-chloro-benzyl, p-bromo-benzyl, or p-nitro-benzyl;
or a pharmaceutically acceptable salt thereof.

21. A pharmaceutical formulation according to claim 20 where the compound is one wherein:
$R_1$ is methyl, ethyl, methoxy, ethoxy, phenyl, benzyl;
or a pharmaceutically acceptable salt thereof.

22. A pharmaceutical formulation according to claim 21 where the compound is one wherein:
$R_1$ is methyl or methoxy;
or a pharmaceutically acceptable salt thereof.

23. A pharmaceutical formulation according to claim 22 where the compound is one wherein:

Z is a bond;
$R_4$ is phenyl substituted by n-pentoxy; and
$R_1$ is methyl;
or a pharmaceutically acceptable salt thereof.

24. A method of inhibiting fungal activity comprising contacting a compound of claim 1 with a fungus.

25. A method according to claim 24 where the compound is one wherein:
R', R", and R'" are each methyl;
$R^{y1}$, $R^{y2}$, $R^{y3}$, $R^{y4}$ are each hydroxy;
or a pharmaceutically acceptable salt thereof.

26. A method according to claim 25 where the compound is one wherein:
$R^{x1}$ and $R^{x2}$ are hydrogen;
or a pharmaceutically acceptable salt thereof.

27. A method according to claim 26 where the compound is one wherein:
$R_2$ is a group of the formula

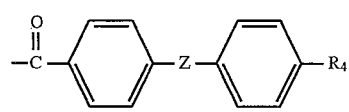

or a pharmaceutically acceptable salt thereof.

28. A method according to claim 27 where the compound is one wherein:
$R_4$ is $C_2$–$C_{12}$ alkynyl, $C_2$–$C_{12}$ substituted alkynyl, $C_1$–$C_{12}$ alkoxy, or phenyl; or
$R_4$ is phenyl substituted by $C_1$–$C_{12}$ alkoxy, or a group of the formula —O—$(CH_2)_2$—O—$(C_1$–$C_6$ alkyl); or
$R_4$ is —$Y^1$—$R_6$;
$Y^1$ is —C≡C—;
$R_6$ is phenyl substituted with a group of the formula —O—$(CH_2)_2$—O—$(C_1$–$C_6$ alkyl);
or a pharmaceutically acceptable salt thereof.

29. A method according to claim 28 where the compound is one wherein:
$R_1$ is $C_1$–$C_4$ alkyl, $C_1$–$C_4$ alkoxy, phenyl, p-chloro-phenyl, p-bromo-phenyl, or p-nitro-phenyl, benzyl, p-chloro-benzyl, p-bromo-benzyl, or p-nitro-benzyl;
or a pharmaceutically acceptable salt thereof.

30. A method according to claim 29 where the compound is one wherein:
$R_1$ is methyl, ethyl, methoxy, ethoxy, phenyl, benzyl;
or a pharmaceutically acceptable salt thereof.

31. A method according to claim 30 where the compound is one wherein:
$R_1$ is methyl or methoxy;
or a pharmaceutically acceptable salt thereof.

32. A method according to claim 31 where the compound is one wherein:
Z is a bond;
$R_4$ is phenyl substituted by n-pentoxy; and
$R_1$ is methyl;
or a pharmaceutically acceptable salt thereof.

33. A method according to claim 30 where the fungus is *Candida albicans*.

34. A method according to claim 30 where the fungus is *Aspergillus fumigatus*.

35. A method of treating a fungal infection which comprises administering an effective amount of a compound of claim 1 to a host in need of such treatment.

36. A method according to claim 35 where the compound is one wherein:

R', R", and R'" are each methyl;

R$^{y1}$, R$^{y2}$, R$^{y3}$, R$^{y4}$ are each hydroxy;

or a pharmaceutically acceptable salt thereof.

37. A method according to claim 36 where the compound is one wherein:

R$^{x1}$ and R$^{x2}$ are hydrogen;

or a pharmaceutically acceptable salt thereof.

38. A method according to claim 37 where the compound is one wherein:

R$_2$ is a group of the formula

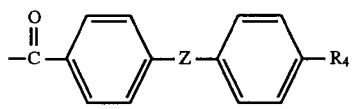

Z is —C≡C— or a bond;

or a pharmaceutically acceptable salt thereof.

39. A method according to claim 38 where the compound is one wherein:

R$_4$ is C$_2$-C$_{12}$ alkynyl, C$_2$-C$_{12}$ substituted alkynyl, C$_1$-C$_{12}$ alkoxy, or phenyl; or R$_4$ is phenyl substituted by C$_1$-C$_{12}$ alkoxy, or a group of the formula —O—(CH$_2$)$_2$—O—(C$_1$-C$_6$ alkyl); or R$_4$ is —Y$^1$—R$_6$;

Y$^1$ is —C≡C—;

R$_6$ is phenyl substituted with a group of the formula —O—(CH$_2$)$_2$—O—(C$_1$-C$_6$ alkyl);

or a pharmaceutically acceptable salt thereof.

40. A method according to claim 39 where the compound is one wherein:

R$_1$ is C$_1$-C$_4$ alkyl, C$_1$-C$_4$ alkoxy, phenyl, p-chloro-phenyl, p-bromo-phenyl, or p-nitro-phenyl, benzyl, p-chloro-benzyl, p-bromo-benzyl, or p-nitro-benzyl;

or a pharmaceutically acceptable salt thereof.

41. A method according to claim 40 where the compound is one wherein:

R$_1$ is methyl, ethyl, methoxy, ethoxy, phenyl, benzyl;

or a pharmaceutically acceptable salt thereof.

42. A method according to claim 41 where the compound is one wherein:

R$_1$ is methyl or methoxy;

or a pharmaceutically acceptable salt thereof.

43. A method according to claim 42 where the compound is one wherein:

Z is a bond;

R$_4$ is phenyl substituted by n-pentoxy; and

R$_1$ is methyl;

or a pharmaceutically acceptable salt thereof.

44. A method according to claim 41 where the fungal infection is *Candida albicans*.

45. A method according to claim 41 where the fungal infection is *Aspergillus fumigatus*.

46. A method for inhibiting parasitic activity comprising contacting a compound of claim 1 with a parasite.

47. A method according to claim 46 where the compound is one wherein:

R', R", and R'" are each methyl;

R$^{y1}$, R$^{y2}$, R$^{y3}$, R$^{y4}$ are each hydroxy;

or a pharmaceutically acceptable salt thereof.

48. A method according to claim 47 where the compound is one wherein:

R$^{x1}$ and R$^{x2}$ are hydrogen;

or a pharmaceutically acceptable salt thereof.

49. A method according to claim 48 where the compound is one wherein:

R$_2$ is a group of the formula

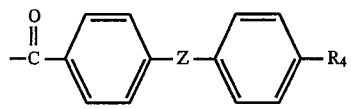

Z is —C≡C— or a bond;

or a pharmaceutically acceptable salt thereof.

50. A method according to claim 49 where the compound is one wherein:

R$_4$ is C$_2$-C$_{12}$ alkynyl, C$_2$-C$_{12}$ substituted alkynyl, C$_1$-C$_{12}$ alkoxy, or phenyl; or R$_4$ is phenyl substituted by C$_1$-C$_{12}$ alkoxy, or a group of the formula —O—(CH$_2$)$_2$—O—(C$_1$-C$_6$ alkyl); or R$_4$ is —Y$^1$—R$_6$;

Y$^1$ is —C≡C—;

R$_6$ is phenyl substituted with a group of the formula —O—(CH$_2$)$_2$—O—(C$_1$-C$_6$ alkyl);

or a pharmaceutically acceptable salt thereof.

51. A method according to claim 50 where the compound is one wherein:

R$_1$ is C$_1$-C$_4$ alkyl, C$_1$-C$_4$ alkoxy, phenyl, p-chloro-phenyl, p-bromo-phenyl, or p-nitro-phenyl, benzyl, p-chloro-benzyl, p-bromo-benzyl, or p-nitro-benzyl;

or a pharmaceutically acceptable salt thereof.

52. A method according to claim 51 where the compound is one wherein:

R$_1$ is methyl, ethyl, methoxy, ethoxy, phenyl, benzyl;

or a pharmaceutically acceptable salt thereof.

53. A method according to claim 52 where the compound is one wherein:

R$_1$ is methyl or methoxy;

or a pharmaceutically acceptable salt thereof.

54. A method according to claim 53 where the compound is one wherein:

Z is a bond;

R$_4$ is phenyl substituted by n-pentoxy; and

R$_1$ is methyl;

or a pharmaceutically acceptable salt thereof.

55. A method according to claim 52 where the parasite is *Pneumcystis carinii*.

56. A method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment.

57. A method according to claim 56 where the compound is one wherein:

R', R", and R'" are each methyl;

R$^{y1}$, R$^{y2}$, R$^{y3}$, RY$^4$ are each hydroxy;

or a pharmaceutically acceptable salt thereof.

58. A method according to claim 57 where the compound is one wherein:

R$^{x1}$ and R$^{x2}$ are hydrogen;

or a pharmaceutically acceptable salt thereof.

59. A method according to claim 58 where the compound is one wherein:

$R_2$ is a group of the formula

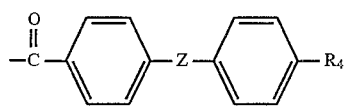

Z is —C≡C— or a bond;
or a pharmaceutically acceptable salt thereof.

60. A method according to claim 59 where the compound is one wherein:

$R_4$ is $C_2$–$C_{12}$ alkynyl, $C_2$–$C_{12}$ substituted alkynyl, $C_1$–$C_{12}$ alkoxy, or phenyl; or $R_4$ is phenyl substituted by $C_1$–$C_{12}$ alkoxy, or a group of the formula —O—$(CH_2)_2$—O—($C_1$–$C_6$ alkyl); or $R_4$ is —$Y^1$—$R_6$;
$Y^1$ is —C≡C—;
$R_6$ is phenyl substituted with a group of the formula —O—$(CH_2)_2$—O—($C_1$–$C_6$ alkyl);
or a pharmaceutically acceptable salt thereof.

61. A method according to claim 60 where the compound is one wherein:

$R_1$ is $C_1$–$C_4$ alkyl, $C_1$–$C_4$ alkoxy, phenyl, p-chloro-phenyl, p-bromo-phenyl, or p-nitro-phenyl, benzyl, p-chloro-benzyl, p-bromo-benzyl, or p-nitro-benzyl;
or a pharmaceutically acceptable salt thereof.

62. A method according to claim 61 where the compound is one wherein:

$R_1$ is methyl, ethyl, methoxy, ethoxy, phenyl, benzyl;
or a pharmaceutically acceptable salt thereof.

63. A method according to claim 62 where the compound is one wherein:

$R_1$ is methyl or methoxy;
or a pharmaceutically acceptable salt thereof.

64. A method according to claim 63 where the compound is one wherein:

z is a bond;
$R_4$ is phenyl substituted by n-pentoxy; and
$R_1$ is methyl;
or a pharmaceutically acceptable salt thereof.

* * * * *

UNITED STATES PATENT AND TRADEMARK OFFICE
CERTIFICATE OF CORRECTION

PATENT NO. : 5,646,111
DATED : July 8, 1997
INVENTOR(S) : Borromeo, et al

It is certified that error appears in the above-identified patent and that said Letters Patent is hereby corrected as shown below:

Column 2, line 61, "$C_7$-$C_1$" should read --$C_7$-$C_{14}$--.
Column 13, line 7, "$O(CH_2)_3$–N" should read --$O(CH_2)_3$·N--.
Column 25, line 37, "N–$R^*_2$" should read --N–$R_2$--.
Column 33, line 58, "$SO_3$–CH " should read --$SO_3$–$CH_2$--
Column 74, line 60, "85," should read --8B,--.
Column 74, line 65, "acid→→50%" should read --acid→50%--.
Column 88, line 19, "$R_2$ is a group of the formula" should read --$R_2$ is a group of the formula Z is -C≡C- or a bond;--.

Signed and Sealed this

Eighth Day of September, 1998

Attest:

BRUCE LEHMAN

Attesting Officer

Commissioner of Patents and Trademarks